United States Patent
Zimmermann et al.

(10) Patent No.: US 10,894,946 B2
(45) Date of Patent: Jan. 19, 2021

(54) MULTILOOP ENGINEERED HEART MUSCLE TISSUE

(71) Applicant: Tissue Systems Holding GmbH, Göttigen (DE)

(72) Inventors: Wolfram-Hubertus Zimmermann, Hamburg (DE); Thomas Eschenhagen, Hamburg (DE)

(73) Assignee: Tissue Systems Holding GmbH, Göttigen (DE)

( * ) Notice: Subject to any disclaimer, the term of this patent is extended or adjusted under 35 U.S.C. 154(b) by 0 days.

(21) Appl. No.: 16/676,064

(22) Filed: Nov. 6, 2019

(65) Prior Publication Data

US 2020/0140820 A1     May 7, 2020

Related U.S. Application Data

(63) Continuation of application No. 15/935,912, filed on Mar. 26, 2018, now Pat. No. 10,494,605, which is a continuation of application No. 14/682,553, filed on Apr. 9, 2015, now Pat. No. 9,957,483, which is a continuation of application No. 12/092,921, filed as application No. PCT/EP2006/010705 on Nov. 8, 2006, now abandoned.

(30) Foreign Application Priority Data

Nov. 8, 2005 (EP) .................................. 05400038

(51) Int. Cl.
| | |
|---|---|
| *C12N 5/077* | (2010.01) |
| *C12M 3/00* | (2006.01) |
| *C12M 1/42* | (2006.01) |

(52) U.S. Cl.
CPC ........... *C12N 5/0657* (2013.01); *C12M 21/08* (2013.01); *C12M 35/04* (2013.01); *C12N 2506/02* (2013.01)

(58) Field of Classification Search
CPC .. C12N 5/0657; C12N 2506/02; C12M 21/08; C12M 35/04
See application file for complete search history.

(56) References Cited

U.S. PATENT DOCUMENTS

| | | | |
|---|---|---|---|
| 7,618,452 B2 * | 11/2009 | Eschenhagen | C12M 21/08 424/93.1 |
| 2003/0003089 A1 | 1/2003 | Akins | |

FOREIGN PATENT DOCUMENTS

| | | |
|---|---|---|
| WO | WO-2001/055297 A2 | 8/2001 |
| WO | WO-2003/007795 A2 | 1/2003 |

OTHER PUBLICATIONS

Assmus et al., Transplantation of progenitor cells and regeneration enhancement in acute myocardial infarction, *Circulation*. 106: 3009-3017 (2002).
Badorff et al., Transdifferentiation of blood-derived human adult endothelial progenitor cells into functionally active cardiomyocytes, *Circulation*. 107:1024-1032 (2003).
Beltrami et al., Adult cardiac stem cells are multipotent and support myocardial regeneration, *Cell*. 114: 763-776 (2003).
Boiani et al., Activity of the germline-specific Oct4-GFP transgene in normal and clone mouse embryos, *Methods Mol. Biol*. 254: 1-34 (2004).
Condorelli et al., Cardiomyocytes induce endothelial cells to transdifferentiate into cardiac muscle: Implications for myocardium regeneration, *Proc. Natl. Acad. Sci. USA*. 98: 10733-10738 (2001).
Cowan et al., Nuclear reprogramming of somatic cells after fusion with human embryonic stem cells, *Science*. 309:1369-1367 (2005).
Dhein et al., Comparative study on the proarrhythmic effects of some antiarrhythmic agents, *Circulation*. 87: 617-630 (1993).
Dimmeler et al. Unchain my heart: The scientific foundations of cardiac repair, *J. Clin. Invest*. 115: 572-583 (2005).
Eiges et al., Establishment of human embryonic stem cell-transfected clones carrying a marker for undifferentiated cells, *Curr. Biol*. 11: 514-518 (2001).
Eschenhagen et al., Three-dimensional reconstitution of embryonic cardiomyocytes in a collagen matrix: A new heart muscle model system, *FASEB J*. 11: 683-694 (1997).
Etzion et al., Cellular cardiomyoplasty of cardiac fibroblasts by adenoviral delivery of MyoD ex vivo: An unlimited source of cells for myocardial repair, *Circulation*. 106: I-125-I-130 (2002).
Fink et al., Chronic stretch of engineered heart tissue induces hypertrophy and functional improvement, *FASEB J*. 14: 669-679 (2000).
Gepstein, Derivation and potential applications of human embryonic stem cells, *Circ. Res*. 91: 866-876 (2002).
Guan et al., Pluripotency of spermatogonial stem cells from adult mouse testis, *Nature*. 440:1199-1203 (2006).
Hosler et al., An octamer motif contributes to the expression of the retinoic acid-regulated zinc finger gene Rex-1 (Zfp-42) in F9 teratocarcinoma cells, *Mol. Cell. Biol*. 13: 2919-2928 (1993).
International Search Report, PCT/EP2006/010705, European Patent Office, dated Mar. 5, 2007.
Jackson et al., Regeneration of ischemic cardiac muscle and vascular endothelium by adult stem cells, *J. Clin. Invest*. 107: 1395-1402 (2001).
Kehat et al., Human embryonic stem cells can differentiate into myocytes with structural and functional properties of cardiomyocytes, *J. Clin. Invest*. 108: 407-414 (2001).

(Continued)

*Primary Examiner* — Aaron J Kosar
(74) *Attorney, Agent, or Firm* — Marshall, Gerstein & Borun LLP

(57) ABSTRACT

The invention is directed to a method for the preparation of a multiring engineered heart tissue construct suitable for use in cardiac tissue augmentation and/or replacement therapy. The invention further refers to multiring EHT constructs which comprise at least two force-generating engineered heart tissue rings fused with each other and a device for preparing the same. Finally, the invention relates to force-generating engineered heart tissue rings derived from human cells and their use in drug screening and target validation assays.

9 Claims, 12 Drawing Sheets

(56) References Cited

OTHER PUBLICATIONS

Klimanskaya et al., Human embryonic stem cell lines derived from single blastomeres, *Nature.* 444: 481-485 (2006).

Klug et al., Genetically selected cardiac myocytes from differentiating embryonic stem cells form stable intracardiac grafts, *J. Clin. Invest.* 98: 216-224 (1996).

Laugwitz et al., Postnatal isl1+cardioblasts enter fully differentiated cardiomyocyte lineage, *Lett. Nature.* 433: 647-653 (2005). Corregendum vol. 446: 934.

Li et al., Natural history of fetal rat cardiomyocytes transplanted into adult rat myocardial scar tissue, *Circulation.* 96: II-179-II-187 (1997).

Lockett et al., Relative efficiency of tumor cell killing in vitro by two enzyme-prodrug systems delivered by identical adenovirus vectors, *Clin. Cancer Res.* 3: 2075-2080 (1997).

Ma et al., High-level sustained transgene expression in human embryonic stem cells using lentiviral vectors, *Stem Cells.* 21: 111-117 (2003).

Menasche et al., Myoblast transplantation for heart failure, *Lancet.* 357: 279-280 (2001).

Messina et al., Isolation and expansion of adult cardiac stem cells from human and murine heart, *Circ. Res.* 95: 911-921 (2004).

Muller et al., Selection of ventricular-like cardiac myocytes from ES cells in vitro, *FASEB J.* 14: 2540-2548 (2000).

Muller-Ehmsen et al., Rebuilding a damaged heart: Long term survival of transplantated neonatal rat cardiomyocytes after myocardial infarction and effect on cardiac function, *Circulation.* 105: 1720-1726 (2002).

Mummery et al., Differentiation of human embryonic stem cells to cardiac myocytes: Role of co-culture with visceral endoderm-like cells, *Circulation.* 107: 2733-2740 (2003).

Murry et al., Cell-based cardiac repair, *Circulation.* 112: 3174-3183 (2005).

Nagy et al., Manipulating the Mouse Embryo: A Laboratory Manual. 431-437 (2002).

Naito et al., Optimizing engineered heart tissue for therapeutic applications as surrogate heart muscle, *Circulation.* 114: 172-8 (2006).

Oh et al., Cardiac progenitor cells from adult myocardium: Homing, differentiation, and fusion after infraction, *Proc. Natl. Acad. Sci.* 100: 12313-12318 (2003).

Olson, A decade of discoveries in cardiac biology, *Nat. Med.* 10: 467-474 (2004).

Orlic et al., Bone marrow cells regenerate infarcted myocardium, *Nature.* 410: 701-705 (2001).

Orlic et al., Mobilized bone marrow cells repair the infracted heart, improving function and survival, *Proc. Natl. Acad. Sci. USA.* 98: 10344-10349 (2001).

Reinecke et al., Survival, integration, and differentiation of cardiomyocyte grafts. A study in normal and injured rat hearts, *Circulation.* 100: 193-202 (1999).

Reinlib et al., Cell transplantation as future therapy for cardiovascular disease? A workshop of the national heart, lung, and blood institute, *Circulation.* 101: E182-E187 (2000).

Sakai et al., Cradiothoracic transplantation, *J. Thorac. Cardiovasc. Surg.* 118: 715-724 (1999).

Sambrook et al., Protocol 1: The basic polymerase chain reaction. Molecular Cloning: A Laboratory Manual, 8.18-8.22 (2001).

Sambrook et al., Protocol 32: Hybridization of bacterial DNA on filters. Molecular Cloning: A Laboratory Manual, 1.138-1.142 (2001).

Shimizu et al., Fabrication of Pulsatile Cardiac Tissue Grafts Using a Novel 3-Dimensional Cell Sheet Manipulation Technique and Temperature-Responsive Cell Culture Surfaces, *Circulation Research.* 90: e40-e48 (2002).

Soonpaa et al., Formation of nascent intercalated disks between grafted fetal cardiomyocytes and host myocardium, *Science.* 264: 98-101 (1994).

Stamm et al., Autologous bone-marrow stem-cell transplantation for myocardial regeneration, *Lancet.* 361: 45-46 (2003).

Strauer et al., Repair of infracted myocardium by autologous intracoronary mononuclear bone marrow cell transplantation in humans, *Circulation.* 106: 1913-1918 (2002).

Takahashi et al., Induction of pluripotent stem cells from mouse embryonic and adult fibroblast cultures by defined factor, *Cell.* 126: 663-676 (2006).

Taylor et al., Regenerating functional myocardium,: Improved performance after skeletal myoblast transplantation, *Nat. Med.* 4: 929-933 (1998).

Thomson et al., Embryonic stem cell lines derived from human blastocysts, *Science.* 282:1145-1147 (1998).

Vrana et al., Nonhuman primate parthenogenetic stem cells, *Proc. Natl. Acad. Sci. USA.* 100: Suppl 1: 11911-11916 (2003).

Wakayama et al., Differentiation of embryonic stem cell lines generated from adult somatic cells by nuclear transfer, *Science.* 292: 740-743 (2001).

Written Opinion of the International Searching Authority, PCT/EP2006/010705, European Patent Office, dated Mar. 5, 2007.

Xu et al., Characterization and enrichment of cardiac myocytes derived from human embryonic stem cells, *Circ. Res.* 91: 501-508 (2002).

Zimmermann et al., Cardiac grafting of engineered heart tissue in syngenic rats, *Circulation.* 106: I-151-I-157 (2002).

Zimmermann et al., Cardiac tissue engineering for replacement therapy, *Heart Fail. Rev.* 8: 259-269 (2003).

Zimmermann et al., Engineered heart tissue for regeneration of diseased hearts, *Biomaterials.* 25: 1639-47 (2004).

Zimmermann et al., Engineered heart tissue grafts improve systolic and diastolic function in infarcted rat hearts, *Nat. Med.* 12:452-8 (2006).

Zimmermann et al., Three-dimensional engineered heart tissue from neonatal rat cardial myocytes, *Biotech.Bioeng.* 68:106-114 (2000).

Zimmermann et al., Tissue engineering of a differentiated cardiac muscle construct, *Circ. Res.* 90: 223-230 (2002).

\* cited by examiner

FIG. 2A  FIG. 2B  FIG. 2C 
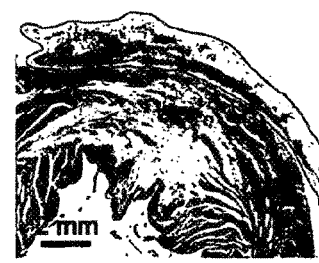  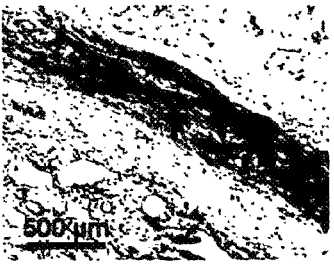
FIG. 2D     FIG. 2E     FIG. 2F

FIG. 7A Echocardiography data:

| | Healthy controls | Infarct baseline | | | Final examination | |
|---|---|---|---|---|---|---|
| | Age matched | Mean of all | Sham | EHT | Sham | EHT |
| n | 29 | 33 | 15 | 18 | 15 | 18 |
| HR (bpm) | 395±33 | 343±28 | 334±23 | 351±31 | 348±18 | 355±35 |
| LVEDD (mm) | 7.6±0.6 | 9.3±0.8 | 9.3±0.8 | 9.3±0.5 | 10.0±1.0 * | 9.3±0.9 § |
| LVESD (mm) | 4.4±0.5 | 7.8±1.0 | 8.1±1.7 | 7.6±0.9 | 8.5±1.4 | 7.9±1.1 |
| FS (%) | 42±6 | 16±9 | 13±10 | 18±7 | 15±8 | 14±12 |
| LVEDA (mm²) | 48±5 | 77±12 | 79±2 | 76±9 | 175±105 * | 179±76 * |
| LVESA (mm²) | 17±3 | 54±11 | 50±12 | 54±9 | 130±78 * | 124±52 * |
| FAS (%) | 64±6 | 30±5 | 29±5 | 30±5 | 25±11 | 30±9 |

Abbreviations:
HR, heart rate; LV, left ventricular; EDD, end-diastolic diameter; ESD, end-systolic diameter; FS, fractional shortening; EDA, end-diastolic area; ESA, end-systolic area; FAS, fractional area shortening; n, group size All data are expressed as mean±SD.
Data from healthy control animals were recorded independently.
Rats that did not survive the complete study duration (6 from 24 in the EHT group and 2 from 17 in the Sham group) were excluded from the data evaluation.
Sham and EHT groups did not show any significant differences at baseline ECHO (infarct baseline).
* $P < 0.05$ vs. infarct baseline (paired t-test); § $P < 0.05$ vs. Sham (unpaired t-test)

FIG. 7B

Magnetic resonance imaging data:

|  | Healthy controls | 2 weeks after LAD ligation | Sham | EHT |
|---|---|---|---|---|
| n | 29 | 8 | 13 | 15 |
| LVAWd (mm) | 1.7±0.4 | 1.0±0.5 | 1.2±0.2 | 1.3±0.2 |
| LVAWs (mm) | 2.8±0.4 | 1.0±0.4 | 1.2±0.3 | 1.7±0.6 * |
| AWThF (%) | 41±13 | 7±15 | -7±28 | 18±19 * |
| LVPWd (mm) | 1.7±0.4 | 1.8±0.2 | 1.5±0.3 | 1.5±0.4 |
| LVPWs (mm) | 3.0±0.5 | 3.1±0.5 | 2.0±0.5 | 2.3±0.6 |
| PWThF (%) | 43±11 | 42±10 | 17±26 | 30±17 |
| Max. LV volume (µl) | 256±45 | 872±148 | 1014±282 | 806±231 * |
| Min. LV volume (µl) | 51±18 | 487±129 | 670±262 | 586±279 |

Abbreviations:
LV, left ventricular; d, diastole; s, systole; AW, anterior wall; PW, posterior wall; ThF, thickening fraction; n, group size All data are expressed as mean±SD.
MRI data was derived from healthy (29 from 29), Sham (13 from 15), and EHT (15 from 18) animals that had been subjected to echocardiography (see Supplement Table I). An independent group of rats (n=8) was subjected to MRI 2 weeks after LAD ligation. MRI could not be performed in 2 of 15 animals from the Sham and 3 of 18 animals from the EHT groups for technical reasons. Except in healthy controls, all animals were subjected to 4D CINE mode MRI to assess volume parameters. Volumes were calculated from short and long axis views in healthy controls. The latter leads to an underestimation of LV volume by approximately twofold (Zimmermann et al. Unpublished). * $P < 0.05$ vs. Sham (unpaired t-test)

FIG. 7C  Hemodynamic data:

|  | Healthy controls | 2 weeks after LAD ligation | Sham | EHT |
|---|---|---|---|---|
| n | 7 | 11 | 8 | 6 |
| HR (bpm) | 312±53 | 318±33 | 294±25 | 297±17 |
| LVEDV (µl) | 383±82 | 634±171 | 978±248 | 713±169 * |
| LVESV (µl) | 208±82 | 536±165 | 727±281 | 509±143 |
| SV (µl) | 261±46 | 165±69 | 384±76 | 289±97 |
| EF (%) | 62±9 | 26±10 | 38±6 | 39±10 |
| LVESP (mmHg) | 76±5 | 70±16 | 82±12 | 82±19 |
| LVEDP (mmHg) | 8±3 | 11±6 | 23±10 | 11±5 * |
| CO (ml/min) | 79±15 | 53±24 | 112±20 | 86±28 |
| SW (mmHg*ml) | 17±4 | 9±6 | 19±6 | 17±5 |
| Ea (mmHg/µl) | 0.30±0.06 | 0.46±0.12 | 0.22±0.05 | 0.32±0.17 |
| +dP/dt (mmHg/sec) | 4939±992 | 3499±1372 | 3040±800 | 3075±1008 |
| -dP/dt (mmHg/sec) | -5171±1281 | -3389±1676 | -2586±543 | -2897±886 |
| +dV/dt (ml/sec) | 9±3 | 9±4 | 12±4 | 14±8 |
| -dV/dt (ml/sec) | -8±2 | -6±3 | -9±2 | -8±5 |
| τ Weiss (msec) | 10±2 | 14±4 | 20±5 | 9±6 * |

Abbreviations:
HR, heart rate; LV, left ventricular; EDV, end-diastolic volume; ESV, end-systolic volume; SV, stroke volume; EF, ejection fraction; EDP, end-diastolic pressure; ESP, end-systolic pressure; CO, cardiac output; SW, stroke work; Ea, arterial elastance; dP/dt, change in pressure/change in time; dV/dt, change in volume/change in time; n, group size All data are presented as mean±SD.
CATH data of healthy and infarcted rats were recorded in an indepent series of experiments. CATH in Sham and EHT animals was performed in a subset of rats that also underwent ECHO and MRI. Volume calibration was performed by equating catheter-recorded minimal and maximal conductance with minimal and maximal 4D MRI-volumes.
* $P < 0.05$ vs. Sham (unpaired t-test)

FIG. 11

Serum free culture medium

| Basic supplements | Growth factor supplements |
|---|---|
| 20% M199 | 20 ng/ml insulin like growth factor-1 |
| 10 nmol/l retinoic acid | 10 ng/ml epidermal growth factor |
| 0,1 nmol/l triiodothyronine | 10 ng/ml fibroblast growth factor-2 |
| 5 µg/ml hydrocortisone | 0,25 ng/ml endothelin-1 |
| 10 µg/ml insulin | 1 µg/ml angiotensin-II |
| 5,5 mg/l transferrin | 10 ng/ml cardiotrophin-1 |
| 5 µg/l selenium | 10 ng/ml interleukin-1β |
| 0,5 µg/l bovine serum albumin | 5 ng/ml transforming growth factor β 1 |
| 4,7 µg/ml linoleic acid | |
| 4,7 µg/ml oleic acid | |

MULTILOOP ENGINEERED HEART MUSCLE TISSUE

FIELD OF THE INVENTION

The invention is directed to a method for the preparation of a multiring engineered heart tissue construct suitable for use in cardiac tissue augmentation and/or replacement therapy. The invention further refers to multiring EHT constructs which comprise at least two force-generating engineered heart tissue rings fused with each other and a device for preparing the same. Finally, the invention relates to force-generating engineered heart tissue rings derived from human cells and their use in drug screening and target validation assays.

BACKGROUND OF THE INVENTION

Myocardial infarction and heart failure represent the main cause of death in industrialized countries. The loss of terminally differentiated cardiac myocytes which is associated with these pathologies accounts for a decrease in myocardial function which can lead to total organ failure or trigger compensatory mechanisms like hypertrophy of the remaining myocardium, activation of neurohumoral systems, and autokrine/parakrine stimulation by various growth factors/cytokines.

It has been shown that endogenous regenerative mechanisms do not suffice to compensate for cardiac myocyte death after myocardial infarction. Modern pharmacotherapy can delay, but not reverse the natural course of the disease. Thus, exogenous regenerative strategies including cardiac implantation or coronary transfusion of cells, activation of endogenous cardiac regeneration by pharmacological means, or implantation of performed, engineered cardiac tissues have gained increasing attention (Reinlib, L. & Field, L., Circulation 101, E182-7 (2000); Zimmermann, W. H. & Eschenhagen, T., Heart Fail Rev 8, 259-69 (2003); Olson, E. N., Nat Med 10, 467-74 (2004); Orlic, D. et al., Proc Nati Acad Sci USA 98, 10344-9 (2001)).

So far, cells of various origins and developmental stages have been grafted into healthy and diseased hearts, including immature cardiac myocytes (Reinecke, H., Zhang, M., Bartosek, T. & Murry, C. E.; Circulation 100, 193-202 (1999); Muller-Ehmsen, J. et al., Circulation 105, 1720-6 (2002); Li, R. K. et al., Circulation 96, 11-179-86; discussion 186-7 (1997)), skeletal myoblasts (Taylor, D. A. et al., Nat Med 4, 929-33 (1998); Menasche, P. et al., Lancet 357, 279-80 (2001)), fibroblasts (Etzion, S. et al., Circulation 106, 1125-30 (2002); Sakai, T. et al., J Thorac Cardiovasc Surg 118, 715-24 (1999)), endothelial cells (Condorelli, G. et al., Proc Natl Acad Sci USA 98, 10733-8 (2001)), embryonic stem cell-derived cardiac myocytes (Soonpaa, M. H., Koh, G. Y., Klug, M. G. & Field, L. J., Science 264, 98-101 (1994)), and a number of potential cardiac progenitors from peripheral blood (Assmus, B. et al., Circulation 106, 3009-17 (2002)) or bone marrow (Orlic, D. et al., Nature 410, 701-5 (2001); Stamm, C. et al., Lancet 361, 45-6 (2003); Strauer, B. E. et al., Circulation 106, 1913-8 (2002)). Even though the evidence for the formation of true cardiac muscle tissue, electrically coupled to the host myocardium is sparse, most studies reported procedure-induced improvement of contractile function after cryo-injury or myocardial infarction.

A different concept in cardiac regeneration is to graft heart muscle produced ex vivo by tissue engineering. Tissue engineering aims at generating functional 3-dimensional tissues outside of the body that can by tailored in size, shape and function according to the respective needs before implanting them into the body. In contrast to cell implantation in preexisting structures, this approach may allow for complete replacement of diseased myocardium or reconstitution of missing cardiac structures in individuals with cardiac malformations.

Despite its potential, cardiac tissue engineering is still in its infancy for several reasons: (i) Postnatal cardiac myocytes do not or not sufficiently replicate. Given the high absolute numbers of cells needed for cardiac regeneration (Gepstein, L., Circ Res 91, 866-76 (2002)), utilisation of primary cardiac myocytes will not be feasible. (ii) To repair myocardial infarctions or correct heart defects, heart tissue patches need to be engineered at a size and with contractile features that have a realistic chance to lend significant support to failing hearts. Size as well as function and in vivo survival depend crucially on metabolic supply. Thus, vascularization is likely to be a prerequisite for successful creation and grafting of large cardiac tissue patches. (iii) The heart not only needs systolic strength, but also depends on unimpeded diastolic relaxation. Consequently, engineered heart muscle must exhibit a large compliance, a feature often neglected in classical, scaffold-based tissue engineering approaches. (iv) Finally, any successful tissue engineering concept will depend on structural and electrical integration of implanted tissue into the host myocardium. Recent progress in stem cell research has opened new perspectives for cell sourcing, e.g. from embryonic (Kehat, I. et al., J Clin Invest 108, 407-14 (2001)) or adult stem cells (Beltrami, A. P. et al., Cell 114, 763-76 (2003); Messina, E. et al., Circ Res (2004)).

Several publications describe the generation of engineered heart tissue in different geometrical sizes and shapes (Zimmermann, W. H. et al., Circ Res 90, 223-30 (2002); Fink, C. et al., Faseb J 14, 669-79 (2000); see also published International Application WO 01/55297). It was shown that engineered heart tissue can be reconstituted by mixing heart cells from rat (including cardiac myocytes, fibroblasts, smooth muscle cells, endothelial cells, macrophages and other cells of leukocytic origin, etc.) with collagen type I, matrigel and serum-containing culture medium (the complete mixture is referred to as reconstitution mix). Specifically, ring-shaped casting molds were used to form ring-shaped EHTs. The engineered tissue rings resemble intact heart tissues in terms of force-frequency behaviour, force-length relationship (FrankStarling mechanism) and response to extracellular calcium (Eschenhagen T, et al., Faseb J. 11, 683-94 (1997); Zimmermann W H et al., Biotechnol Bioeng. 68, 106-14 (2000). These data support the conclusion of true heart tissue-development in vitro from a functional point of view. However, differences exist as well. For example, absolute contractile forces of EHTs remain lower than in the intact heart. In the literature, maximal twitch tensions of about 1-2 $mN/mm^2$ are reported in artificial heart muscle (overview in Zimmermann W H, et al., Heart Fail Rev. 8, 259-69 (2003)). In comparison, papillary muscles from rat develop 4-10 $mN/mm^2$. The difference of EHT force generation as compared to mature heart muscles most likely reflects both a quantitative and a qualitative aspect, as for example a lower fractional occupancy of the EHT tissues by cardiac myocytes and the lower degree of sarcomere development. In fact, single adult cardiac myocytes develop up to 56 $mN/mm^2$ These ideal forces are unlikely to be reached in intact muscle preparations due to the lack of oxygen and metabolite supply in the absence of blood perfusion.

It has been demonstrated that a simple scale-up of the preparation approach, e.g. by use of larger casting molds than those described in International Application WO 01/55297 cannot solve the problem, since size of the engineered tissue constructs appears to be limited by maximum diffusion distances for nutrients and oxygen. Indeed, none of the various tissue engineering approaches developed today generate cardiac tissue-like, contracting constructs of a thickness of more than 0.8 mm (Zimmermann, W. H. et al., Circ Res 90, 223-30 (2002)). Yet, so far developed artificial heart tissues do not represent homogeneous myocardium, but consists of a large fraction of cell-free matrix and interconnected cardiac muscle strands that do not exceed 20-100 µm in thickness. Interconnected muscle strands can be observed and evaluated by confo-cal laser scanning microscopy e.g. after actin or actinin staining as outlined in Zimmermann et al. (Circ Res 90, 223-30 (2002)).

Therefore, a need exists for the provision of improved heart tissue grafts of larger size which overcome the above shortcomings. It has been an object of the present invention to provide heart tissue grafts having a size and contractile strength which allows for the effective support of failing hearts in a mammal, such as a human. The present invention provides for a solution of this problem and offers other related benefits as well.

It has surprisingly been found in course of the invention that large threedimensional tissue grafts which consist of a well-organized and highly differentiated cardiac muscle syncytium can be produced by fusing two or more engineered heart tissue rings with each other. Fusing, as used herein, means that single EHT units or stripes grow together at a region where sustained physical contact is established to form a contiguous cell assembly. The assembly represents a structurally, electrically and functionally syncytium that may be finally used as a cardiac tissue graft in vivo. Such graft constructs are designated "multiring engineered heart tissue construct" herein. Specifically, it has been found that several engineered heart tissue rings or comparable geometric forms can be woven together, thus forming a network in which each individual construct remains accessible for unlimited diffusion and exchange of nutrients. As a consequence, these constructs do not exhibit the typical size limitations known from the prior art. Multiring engineered heart tissue constructs of the invention can be produced by using a plurality of distinct engineered heart tissue rings as those described in the prior art. The rings can be fused in any suitable manner to provide "chainmail"-like constructs. By this technique, the form of the multiring constructs can be adjusted dependent on the specific therapeutic approach. For example, large multiring netlike patches can be generated for replacing dysfunctional areas of the heart of a mammal. Alternatively, bag-like forms may be generated which surround the complete organ. The size of the multiring construct patches can be varied dependent on the size of the area to be treated. The multiring engineered heart tissue construct of the invention can be comprised of force-generating engineered heart tissue rings derived from any mammal. In view of its intended use in the field of tissue augmentation, it is preferred that the engineered heart tissue rings are derived from human cells.

Thus, according to a first aspect of the invention, an ex vivo method for the preparation of a multiring engineered heart tissue construct suitable for use in cardiac tissue augmentation and/or replacement therapy is provided, which method comprises the steps of a) providing force-generating engineered heart tissue rings;

b) placing into contact at least two force-generating engineered heart tissue rings so that each force-generating engineered heart tissue ring has one or more contact points to an adjacent force-generating engineered heart tissue ring; and c) culturing the force-generating engineered heart tissue rings under conditions which allow fusion of the at least two force-generating engineered heart tissue rings at the one or more contact points to form a multiring heart tissue construct.

As used herein, the term "multiring engineered tissue construct" means an ex vivo produced tissue construct comprised of at least two, and preferably more than two distinct force-generating engineered heart tissue rings, which may have been produced by tissue engineering techniques, such as those described in Zimmermann, et al., Circ Res 90, 223-30 (2002) and International Application WO 01/55297. The term "tissue" refers to a group of similar cells united to perform a specific function or a grouping of cells that are similarly characterized by their structure and function. The constructs of the invention consist of at least two distinct engineered heart tissue rings. In this context, the expression "multiring" is meant to emphasize that the fused construct comprises a plurality of loop structures originating from the essentially circular shape of the force-generating engineered heart tissue rings that serve as a basis material for the construct of the invention. Such loop structures have been proven very useful for the handling of the tissue construct, for example when surgically fixing the construct to the recipient organ or tissue. Additionally, the term multiring is also intended to comprise embodiments in which tissue constructs are formed which consist of tube- or stripe-like structures. The former might be obtained by establishing side-to-side connections between two or more rings (FIG. 8B). The latter might be obtained by forming a ring structure and subsequently cut the latter in two or more pieces for further use. An example of such tissue construct is provided in FIG. 8C.

The multiring construct according to the present invention comprises force-generating engineered heart tissue rings. The production of such contractile engineered heart tissue in circular/annular shape has been described in detail in the prior art, for example in published International Application WO 01/55297 and in Zimmermann et al., 2000, Biotechnology and Bioengineering Vol. 68, pages 106 to 114. Cardiac myocytes such as those obtained from tissue samples of neonatal hearts of different mammals may be used for preparing the EHT rings, as described in Zimmermann, et al., Circ Res 90, 223-30 (2002) and International application WO 01/55297. As can be taken from these publications, engineered heart tissue rings can be obtained by culturing cardiac myocytes in ring-shaped molding devices. It has been shown that mixed populations consisting of almost identical portions of cardiac myocytes and non-cardiac myocytes result in EHTs with increased contractile properties compared to selected cardiac myocytes (Zimmermann et al. (2003), Heart Failure Rev., 8, 259-269). Fetal or neonatal cardiac myocytes from mammals, such as rat, mouse or primates are a suitable source for obtaining EHT rings. In contrast to differentiated cardiac myocytes, these cells still have the capability to divide as well as to redifferentiate after dedifferentiation. Briefly, a solution of a scaffold substance (such as collagen type I) is mixed with culture medium (final concentration in the mixture: 1×DMEM; 2% chicken embryo extract; 10% horse serum; 100 jig/ml Streptomycin; 100 U/ml penicillin). The pH of the mixture is adjusted to physiologic values . . . 7.4 with 0.1 N NaOH. Engelbreth-Holm-Swarm tumor exudate (also known as "Matrigel") is added to give a final concentration of 5-15%. This mixture is added to a cell suspension of fetal or neonatal cells (for example, 2.5×10⁶ cells/EHT). Alternatively, serum-free media may be used. A serum-free medium suitable for culturing the cardiac myocytes is exemplified in FIG. 12. The person skilled in the art will appreciate that several modifications as to the components of the medium can be performed. Moreover, Matrigel may be substituted against insulin and triiodothyronine, as described in more detail below.

Alternatively, mammalian cardiac myocyte progenitor cells, such as pluripotent stem cells, adult or embryonic, provide a source for preparing the EHT rings. Preferably, the EHT rings to be used in the method according to the invention are derived from human cells. Human engineered heart tissue rings may be obtained by use of circular-shaped casting molds. In this case, cardiac myocyte progenitor cells, such as stem cells, more preferably pluripotent embryonic stem cells, may be used for preparing the force-generating engineered heart tissue rings. However, also other types of stem cells, such as pluripotent adult stem cells may be used. The preparation of contractile EHT rings derived from human stem cells is particularly described in example 6 of the present invention.

The force-generating engineered heart tissue rings produced from human or non-human mammalian cells comprise cardiac myocytes. However, they are usually not composed purely of cardiac myocytes but comprise almost all cells species that are normally found in the heart including cardiac myocytes, fibroblasts, smooth muscle cells, endothelial cells, macrophages and other cells of leukocytotic origin. Typically, the presence of cardiac cells within a given EHT ring can be confirmed by positive staining with anti-cardiac myosin heavy chain, anti-α-actinin, anti-desmin and/or anti-cardiac troponin I antibodies (see Kehat I. et al, supra). If cells are derived from human cells, this can readily be confirmed by well known methods, such as PCR analysis based on typically conserved regions of the genome.

The term "ring" as used in the context of the present invention is meant in a broad sense to comprise also geometric forms which do not represent a perfect geometric ring. For example, it may also comprise other forms which consists of annularly closed tissue tube structures. It has been found that a circular geometry of the EHT is ideal for several technical and biological reasons. For example, circular heart tissue structures allow large scale production with minimal handling. Most importantly, circular engineered heart tissue structures can be easily miniaturized for high-throughput screening and they exhibit better tissue formation than the non-circular designs, since the circular form causes homogeneous force distribution throughout the tissues. Furthermore, nutrient distribution is facilitated in circular-shaped tissues. Also not being particularly restricted to a specific limited size, it has been shown that engineered heart tissue rings having an outer diameter of 8-12 mm have particularly preferred characteristics. The inner diameter of these rings should be in the range of 6-10 mm. Particularly preferred are EHT rings with an outer diameter of about 10 and an inner diameter of about 8 mm (see International Application WO 01/55297).

As used herein, the term "force-generating" means that the engineered heart tissue rings are able to actively contract against a given mechanical load. The intrinsic property of heart cells to form contractile aggregates has been known in the field for years. Several publication reported that contractile properties are maintained when threedimensional EHTs, such as EHTs of circular shape, are constructed. Contraction of the tissue constructs are triggered by addition of $Ca^{2+}$ ions or isoprenaline to the culture medium. Zimmermann, W. H. et al., Circulation 106, I 151-7 (2002), reported determination of contractile functions of engineered tissue rings by isometric force measurements in organ baths before implantation (see FIG. 2a of the above publication). Maximal twitch tension (TT) values of about 0.4 mN to 0.7 mN were measured.

According to a first step of the method for the preparation of the multiring engineered heart tissue construct of the invention, distinct force-generating engineered heart tissue rings are provided. These rings are, for example, obtainable by culturing suitable cells in ring-shaped molding devices. The preparation of such rings from mammalian cell sources is described in the art, for example, in Zimmermann, et al., Circ Res 90, 223-30 (2002), in International Application WO 01/55297 and in Example 1. Using the same casting molds, engineered heart tissue rings may also be prepared from human stem cells, for example, as described in Example 6.

Subsequently, at least two force-generating engineered heart tissue rings are positioned into contact, so that each of these force-generating engineered heart tissue rings has one or more contact points with at least one further EHT ring in its vicinity. This means, each of the engineered heart tissue rings used for preparing the multiring heart muscle construct is tangent to at least a further engineered heart tissue ring. Preferably, the distinct EHT rings are held via suspension points of a holding device. According to a very simple embodiment of the invention, several force-generating engineered heart tissue rings as defined herein are stacked, i.e. laid upon each other to form a stack with a plurality of loops extending in different directions (see for example FIG. 8A). It is particularly preferred that the force-generating EHT rings are placed into contact by stacking of the distinct rings to form a central region in which the force-generating engineered heart tissue rings overlap with each other as shown in FIG. 8A). According to an alternative embodiment several rings are placed into contact as shown in FIG. 8B. Apart from that, any other random distribution of the tissue rings in which each ring is in contact with at least another one are possible. It has been found in course of the invention, that the tissue rings which have been positioned into contact in this manner fuse and form a complex in-unison contracting construct which is synchronized with respect to its contracting activity. This finding allows for the generation of large tissue-like structures by fusing distinct contractile EHT rings (or prefused multiring structures comprising several of theses EHT rings).

In a further step, the force-generating engineered heart tissue rings, which are in contact with each other, are cultured under conditions which allow the fusion of the contacted ring structures to form an artificial heart muscle construct. For this purpose, the engineered heart tissue rings are normally incubated in culture dishes, wherein the rings are submersed in appropriate culture medium. If a holding device is used for culturing, the device should be designed to allow the tissue rings to stay in continuous contact with the culture medium. The choice of the culture medium is not critical. Conventional media for culturing cardiac myocytes may be used. Such media are known in the art and described, for example, in Zimmermann, W. H. et al., Circulation 106, I 151-7 (2002) and published International Application WO 01/55297. These media may further be modified, i.e. by substituting Matrigel against a mixture of Insulin (10 pg/ml) and triiodothyronine (1 nM). It was found that the addition of insulin and triiodothyronine allowed for the generation of strongly contracting EHTs. Simultaneous addition of both factors for only 24 h at the beginning of the EHT culture was sufficient. By using insulin and triiodothyronine during EHT construction, improved EHT contractility was achieved. These effects did not stem from enhanced overall EHT cell number, since no difference in the DNA content and no apparent structural differences were observed. Rather, the effects may be the result of enhanced protein content or improved survival of cardiomyocytes leading to a higher cardiomyocyte fraction without an apparent change of the overall cell number (standard EHTs on culture day 12 contain roughly 100.000 cardiomyocytes and a total cell number of 600.000; a fractional increase in cardiomyocyte number may have significant effects on force of contraction, may lead to an increase in overall "cardiomyocyte" protein [e.g. sarcomeric actin] but may not lead to a measurable [by total DNA quantification and cell counting after enzymatic digestion of EHTs) increase in total cell number in EHTs treated with insulin and triiodothyronine. Furthermore, the media as used herein for culturing stem cells in example 6 can be used as well.

According to a more preferred embodiment of the invention, the same media which has been used for casting the EHT rings are used during incubation of the force-generating engineered heart tissue rings for fusion (see examples 1 and 6 for neonatal cardiomyocyte and stem cells, respectively). Suitable culturing conditions are described in the art and comprise a physiological temperature range of 30–40° C., preferably 3638° C., and more preferably 37° C. The percentage of $O_2$ in the ambient air should range from 21-80%, preferably 70%, 60% 50%, and more preferably 40%. Culturing may be performed for 3 to 50 days, preferably 10-30 days, and more preferably 15-20 days.

According to preferred embodiment of the present invention a plurality of distinct force-generating engineered heart tissue rings are placed into contact to form the fused multiring EHT construct. Preferably, five or more tissue are placed into contact, for example six, seven, eight, nine, ten, eleven, twelve or more. More preferably, more than 15, 20, 30, 40, 50, or even up to 100 force-generating engineered heart tissue rings are placed into contact to form the fused multiring EHT construct. It has to be understood that larger multiring EHT constructs can also be formed in several steps, for example by forming several constructs of 5-10 EHT rings in a first step and fusing these different constructs in a subsequent step. In any case, care should be taken that the resulting multiring EHT construct is cultured for a further period of time to allow synchronization of contractile activities.

According to preferred embodiment of the present invention, the force-generating engineered heart tissue rings used for preparing the multiring heart muscle construct of the invention are subjected to tensile stress prior to or simultaneously with placing into contact the at least two force-generating engineered heart tissue rings. For example, when using a device of the invention as described in more detail below, placing into contact of the EHT rings and subjecting to tensile stress can be performed in one step. Subjecting to tensile stress can for example be performed by actively stretching the tissue rings, for instance by use of a mechanical stretching device like the one described in Zimmermann, W. H. et al., Circulation Res 90, 223-30 (2002). Such device can provide for a "static" load, i.e. a permanent load produced by expanding the ring by 3 to 20%, preferably 10% of its original length (original length determined in the absence of any load) as described in WO 01/55297. Alternatively, a "phasic" load can be applied by periodically expanding the ring by 3 to 20%, preferably 10% of its original length, for example at a frequency of 0.1-10 Hz, preferably 1-5 Hz. Such stretching can be regarded as a static or phasic manner, respectively.

In several publications, it was demonstrated that contractile properties of artificially synthesized heart tissue rings can be improved by mechanically stretching the rings after their casting (see Eschenhagen et al., 2002; Fink et al., 2000; Zimmermann et al., 2002b). It has been demonstrated that mechanical load improves both orientation and differentiation of muscle cells in EHT rings. Tensile stress can be applied for a period of time ranging from several hours to more than 40 days. Preferably, tensile stress is applied for 5-9, more preferably 7 days. During imposing tensile stress, the EHT rings are cultured under the conditions recited above.

According to a preferred embodiment of the invention, tensile stress is applied by a static, phasic or auxotonic manner or a combination thereof. According to a particularly preferred embodiment of the invention, tensile stress is applied by a auxotonic manner. An "auxotonic manner", as used herein, means that the engineered heart tissue rings are kept under conditions so that they have to contract against a defined force and are reexpanded during relaxation of the EHT ring by another force or, preferably, the same force. For example, if the tissue ring is held under tension by using a spring, this spring will provide a defined force against which the EHT must contract. Upon relaxation of the EHT ring, the spring will expand the EHT ring again. It has been found that culturing the EHT rings in this manner leads to a considerable increase of contractile properties compared to phasic and static processes (see FIG. 1B). Therefore, both the single engineered heart tissue rings as well as the artificial multiring heart muscle construct consisting of the distinct heart tissue rings show improved maximal active forces during contraction. Under auxotonic load, the EHT rings have to perform contraction under conditions which resemble the systole and diastole phase of the heart cycle. In other words, the engineered heart tissue rings are held under conditions which corresponds to the native environment of active heart tissue.

Auxotonic tensile stress can be applied, for example, by elastically suspending each of the at least two force-generating engineered heart tissue rings between at least two associated suspension means wherein at least one of said associated suspension means is resiliently biased (i.e. mounted to be movable against a bias force) so that the individual force-generating EHT rings are able to contract against the bias force provided by the suspension means and are reexpanded during relaxation of the EHT ring. Preferably each of the force-generating engineered heart tissue rings is suspended between two associated suspension means. Preferably, the two suspension means can be variably adjusted to be used with rings of different diameters. The suspension means may be part of a device as explained in detail below. Such device comprises a pair of suspension means for each EHT ring. According to a further embodiment, all of the associated suspension means are resiliently biased.

Preferably, the at least one suspension means can be adjusted to vary the tensile stress. This means, the load applied to the EHT rings can be easily adjusted to a specific strength by modulating the tension provided by the resilient means. For example, springs can be used as resilient means comprising spring coils which can be adjusted in order to modulate the resilient tension of the spring.

As already mentioned, "auxotonic" tensile stress can be applied simultaneously with placing into contact of the at least two force-generating engineered heart tissue rings. For example, the different EHT rings can be suspended in a device as explained in detail below so that the tissue rings are held in a position that provides for a plurality of contact points between the different heart tissue rings. It has been found that the fusion of the different rings at their contact points occurs also during the different rings are subjected to the tensile stress. Surprisingly, subjecting the heart tissue rings to tensile stress in terms of auxotonic (or phasic or static) load obviously does not hamper formation of a fused multiring construct. Therefore, the culturing which allows fusion of the at least two engineered heart tissue rings to form an artificial heart muscle construct can be performed while the heart tissue rings are held under tensile stress.

According to a further aspect, the invention refers to multiring EHT constructs which comprise at least two force-generating engineered heart tissue rings fused with each other to form an interconnected tissue construct. The multiring engineered heart tissue construct is obtainable according to a method described above. As already explained, the multiring constructs can comprise more than 5 EHT rings, for example 15, 20, 30, 40, 50, or even up to 100. Preferably, each of the EHT rings has an outer diameter of 8-12 mm.

Preferably, the multiring EHT constructs of the invention are comprised of fused engineered heart tissue rings which are stacked to form a central region in which the force-generating engineered heart tissue rings overlap with each other. A construct, which results from stacking of five different tissue rings is depicted in FIG. 8A. Further examples of multir-ing EHT construct structures are provided in FIG. 8B and FIG. 8C. FIG. 8B shows a plurality of ring structures which are suspended by a flexible lateral suspension device wherein the distinct ring structures are in contact with each other in the region of contact with the suspension means. It has to be understood by the person ordinary skilled in the art that these examples of ring assemblies are not limiting. A large number of further geometric structures are conceivable for example bag- or net-shaped structures or different forms of stackings.

The multiring heart muscle constructs provided by the present invention show properties which makes them particularly useful for tissue grafts in heart tissue augmentation and/or replacement therapy. In animal models, it has been shown that multiring heart muscle constructs generated from neonatal myocard cells of rats were suitable to provide functional tissue grafts which could be successfully transplanted to infarcted rat hearts and support dysfunctional tissue damaged after myocard infarct (see examples). The multiring engineered heart tissue construct comprise cardiac myocytes, i.e. cells comprising one or more of the following proteins: cardiac myosin heavy chain, α-actinin, desmin and/orcardiac troponin I. It is clear that tissue grafts which are intended to be used in human therapy should be derived from cells of human origin. Therefore, according to preferred embodiment of the present invention, the multiring heart muscle constructs are comprised of force-generating engineered heart tissue rings derived from human cells. The human origin of the EHT can be confirmed by a plurality of different methods known in the art, for example by amplification of species-specific DNA sequences and/or the antibody-based detection of species-specific antigens, such as polypeptides. The preparation of the engineered heart tissue rings starting from human stem cells is exemplified in detail in example 6 of the present invention.

It is preferred that the multiring EHT construct of the invention has a overall twitch tension of more than 2.5 mN, more preferably more than 3 mN, for example 3.5 mN, 4 mN, 4.5 mN, 5 mN, 5.5 mN, 6 mN, 10 mN, 15 mN or more. The capability of the multiring construct to contract can be determined in accordance with methods as described in the prior art, for example, by monitoring the constructs in standard organ baths (see Zimmermann et al., Biotech. Bioeng., 68, (2000)).

According to a further aspect, the invention relates to the use of the multiring EHT construct of the invention for drug target validation and drug development. According to a preferred embodiment, the multiring EHT construct is used in drug screening or target validation assays. In this context, it is preferred that the multiring EHT construct used is derived from a mammal, such as a human. For example, the multiring construct can be used to analyze the capability of candidate drugs to interfere with the physiological function of the native cardiac tissue of a mammal. For this, the capability of said candidate drug to enhance or reduce contractile functions of the multiring EHT construct is determined. Moreover, the multiring EHT construct may be used in determining the influence of the activity of certain genes on the physiological function of the native cardiac tissue of a mammal (referred to herein as target validation). For this purpose, genes of the cells within the distinct EHT rings (or cells which are used for preparing the same) may be knocked-out or overexpressed or otherwise influenced in view of their expression rate (e.g. by addition of inhibitory molecules, such as small interfering RNAs). Genes may be selectively switched on or off, and the alterations in the contractile functions of the multiring EHT construct are determined.

The invention provides a method for providing force-generating engineered heart tissue rings derived from human cells comprising the steps of:
a) providing undifferentiated human embryonic stem cells;
b) culturing said undifferentiated human embryonic stem cells under conditions which allow for propagating the cells;
c) mixing the cells with a suitable scaffold material in a circular casting mold;
d) culturing the human embryonic stem cells under conditions which allow for differentiation of the cells into cardiac myocytes and formation of a tissue ring structure.

The method can be performed by using the cell lines, media and conditions described in example 6 of the present invention. Particularly, the embryonic stem cells may comprise a selection system and may be subjected to selection before or simultaneously with reconstitution of the EHTs. As explained in more detail below, a suitable scaffold material may be collagen type I. As a matter of course, the human force-generating engineered heart tissue rings resulting from the method may also be subjected to tensile stress as described above with respect to the multiring constructs.

Accordingly, the invention further provides a force-generating engineered heart tissue ring derived from human cells, preferably human stem cells. The tissue ring essentially consists of differentiated human cardiac myocytes and other cell types usually found in heart tissue, such as fibroblasts, smooth muscle cells, endothelial cells, cells of leukocytic origin, like macrophages, etc.) which are embedded by a non-cellular matrix. The presence of cardiac myocytes may be confirmed by detecting one or more of the following proteins: cardiac myosin heavy chain, α-actinin, desmin and/orcardiac troponin I.

According to a preferred embodiment, the force-generating engineered heart tissue ring derived from human cells is used in drug screening assays. For example, the EHT ring derived from human cells can be used to analyze the capability of candidate drugs to interfere with the physiological function of the native cardiac tissue of a mammal. For this, the capability of said candidate drug to enhance or reduce contractile functions of the human EHT is determined. Moreover, the force-generating engineered heart tissue ring derived from human cells may be used in determining the influence of the activity of certain genes on the physiological function of the native cardiac tissue of a mammal (referred to herein as target validation). For this purpose, genes of the cells within the EHT ring (or cells which are used for preparing the same) may be knocked-out or overexpressed or otherwise influenced in view of their expression rate (e.g. by addition of inhibitory molecules, such as small interfering RNAs). Genes may be selectively switched on or off, and the alterations in the contractile functions of the human EHT are determined.

According to a further aspect, the invention provides a device for preparing a multiring engineered heart tissue construct, comprising a plurality of associated suspension means for suspending force-generating engineered heart tissue rings under tensile stress, wherein at least one of each of the associated suspension means is resiliently biased so that the suspended force-generating engineered heart tissue ring is able to contract against the bias force provided by the suspension means, wherein the suspension means are arranged to each other so that each force-generating engineered heart tissue ring has one or more contact points to an adjacent force-generating engineered heart tissue ring when suspended in the device. A preferred embodiment of a device according to the invention is depicted in FIG. 10.

Preferably, two suspension means are associated to each other to form a pair of associated suspension means. It is preferred that the device comprises more than two pairs of associated suspension means so that more than two EHT rings can be suspended in the device. Preferably, the device is design for more than 5 EHT rings, for example 15, 20, 30 or even more.

According to a further embodiment, the associated suspension means of the device are arranged to each other so that the force-generating engineered heart tissue rings can be suspended by stacking to form a central region in which the force-generating engineered heart tissue rings overlap with each other.

According to a particularly preferred embodiment, all associated suspension means are resiliently biased. Preferably, at least one suspension means which is resiliently biased can be adjusted to vary the tensile stress.

BRIEF DESCRIPTION OF THE DRAWINGS

In the following the invention is described by way of examples with reference to the accompanying drawings in which:

FIGS. 2A-2F show the multiring EHT construct while being implanted (FIG. 2A) and four weeks after engraftment at different magnification scales (FIG. 2B);

FIGS. 7A-7C show the results from echocardiography (FIG. 7A), magnetic resonance imaging (FIG. 7B) and hemodynamic analysis (FIG. 7C)

FIG. 11 shows the composition of a serum-free culture medium suitable for culturing cardiac myocytes and EHTs under chemically defined conditions.

FIGS. 1A-1F show the influences of oxygen, load, and insulin in isometric contraction experiments in single engineered heart tissue (EHT) rings (TT: twitch tension). Direct comparison of calcium response curves revealed that EHT ring benefited from oxygen supplementation ($O_2$: n=11 at 21%; n=5 at 30%; n=10 at 40%; FIG. 1A), auxotonic (aux.; n=8) in contrast to static (Sta.; n=8) or phasic (Pha.; n=8) load (FIG. 1B), and addition of insulin (10 fag/ml; n=4) when compared to untreated controls (n=3; FIG. 1C). To increase size, 5 EHT rings (FIG. 1D) were stacked in a custom made device that facilitate EHT fusion and contractions under auxotonic load (FIG. 1E), resulting in synchronously contracting multiring EHT constructs (FIG. 1F) ready for in vivo engraftment. *$P<0.05$ vs. 21% $O_2$, static load, and culture in the absence of insulin (Ctr.), respectively by repeated ANOVA. Bars: 10 mm.

FIGS. 2A-2F show the morphology of grafted multiring EHT construct 4 weeks after engraftment. Multiring EHT constructs were implanted through a left lateral thoracotomy (FIG. 2A). Mid-ventricular cross sections of excised hearts 28 days after implantation revealed that engrafted constructs remained pale (FIG. 1B) but were firmly attached to the infarct scar (c). H&E staining of paraffin sections through the infarcted left ventricular free wall 4 weeks after construct engraftment demonstrated the formation of thick cardiac muscle on top of the infarct scar (FIG. 1D; multiring EHT construct encircled). High power magnification of the infarct area showed that engrafted constructs form compact and oriented heart muscle (FIGS. 1E-1F) spanning the transmural infarct.

FIGS. 3A-3K show the identification of grafted cells by in vitro DAPI labelling. Bright light (FIG. 3A) and UV-illuminated (FIG. 3B) images depict a DAPI labelled multiring EHT construct prior to implantation. Higher magnification revealed nuclear DAPI staining (FIG. 3C; magnification of marked area in FIG. 3B). Four weeks after engraftment, cells could readily be distinguished from native myocardium by the blue staining of the donor cell nuclei (low power view; FIG. 3D: actin; FIG. 3E: background; FIG. 3F; nuclei in EHT graft; FIG. 3G: merged image). High resolution laser scanning microscopy revealed the highly differentiated sarcomeric organization of engrafted cardiac myocytes (FIG. 3H: actin-green; nuclei-blue). Moreover, vascularization of grafts was evident (FIG. 3I, arrows in reconstituted confocal images; FIG. 3J, cross section; actin-green, nuclei-blue, actinin-red). Newly formed vessels contained many DAPI-positive cells (FIG. 3K, actin-green). Macrophages (ED2-red) with blue nuclei were found in close proximity to newly formed vessels. Erythrocytes (*) were visualized by differential interference contrast imaging (FIG. 3K).

FIGS. 4A-4C depict results of the electrical integration analysis of grafted multiring EHT constructs in vivo. Epicardial activation time was analyzed in Langendorff-perfused hearts from experimental rats 4 weeks after Sham surgery or multiring EHT construct implantation. 3D plots of representative activation times display the expected delay of epicardial activation in Sham hearts in the area of infarction (FIG. 4A). Activation was restored to physiological values in hearts with grafts (FIG. 4B). Total activation time was assessed for statistical analysis in right, anterior, lateral, and posterior segments of the hearts (FIG. 4C). *$P<0.05$ vs. Sham by ANOVA with Mann-U-Whitney test.

FIGS. 5A-5F show the changes in left ventricular function after multiring EHT construct implantation. Left ventricular end-diastolic diameter (LVEDD; FIG. 5A) and fractional area shortening (FAS; FIG. 5B) determined by ECHO. "Healthy" indicates age-matched untreated controls (n=29). "Infarction" indicates pooled values (n=33) measured 14 days after infarction in those animals that underwent Sham (n=15) and EHT (n=18) surgeries (see FIG. 7A for individual group data). These animals were reevaluated after additional 28 days by ECHO and subsequently subjected to MRI (FIGS. 5C-5F) with 2 and 3 exceptions in multiring EHT construct and Sham groups, respectively, due to technical reasons. Maximal and minimal volumes of the left ventricle were calculated from 4D CINE mode MRI images in multiring EHT construct (n=15) and Sham (n=13) rats and supported the ECHO findings (FIG. 5D). To assess local contractility, systolic thickening in anterior (AWThF; FIG. 5E) and posterior (PWThF; FIG. 5F) segments of the ventricular wall were analyzed. MRI data from healthy rats (n=29) and 2 weeks after infarction (n=8) were recorded in an independent series of experiments and are displayed for comparison. *$P<0.05$ multiring EHT construct vs. Sham by unpaired student's t-test. $P<0.05$ vs. "Infarction" by paired student's t-test.

FIGS. 6A-6D show the influence of multiring EHT construct grafting on left ventricular hemodynamics. Multiring EHT construct engraftment (n=6) resulted in a leftward shift of the pressure-volume relationship indicating an improvement of hemody-namics when compared to Sham (n=8) animals (FIG. 6A; representative pressure-volume loops). In detail analysis of left ventricular enddiastolic volume (LVEDV) and pressure (LVEDP) as well as relaxation (tau) demonstrated a prevention of further dilation (FIG. 6B) and a normalization of LVEDP (FIG. 6C) and tau (FIG. 6D) by multiring EHT construct implantation. CATH data from healthy rats (n=6) and 2 weeks after infarction (n=9) were recorded in an independent series of experiments and are displayed for comparison. *$P<0.05$ multiring EHT construct vs. Sham by unpaired student's t-test.

FIGS. 7A-7C show the results from echocardiography (FIG. 7A), magnetic resonance imaging (FIG. 7B), and hemodynamic analysis (FIG. 7C).

FIGS. 8A-8C show different geometries of multiring EHT constructs according to the invention: (FIG. 8A) star-shaped multiring EHT construct prepared from 5 force-generating engineered cardiac tissue rings by stacking; (FIG. 8B) tubular multiring EHT construct prepared by placing multiple EHT rings in series on a holding device to establish side-to-side contact followed by fusion and formation of synchronously contracting multiring engineered heart tissue construct; (FIG. 8C) alternatively, EHT rings may be cut to yield EHT stripes. The latter may be stacked freely onto each other whilst being held at a defined distance under defined load, which may be static, phasic or auxotonic. This format allows free organization of EHT rings into multiunit engineered heart tissue construct.

FIGS. 9A-9D demonstrate the generation of different EHT geometries. EHTs fuse after sustained contact to form in-unison contracting complex cardiac muscle constructs. Star-shaped EHTs (FIG. 9A) were generated by stacking 5 EHTs on a custom-made holder. Single-unit EHTs fused in the center. 5 EHTs (FIG. 9B) were grown on horizontal glass pipettes. Adjacent EHTs fused to form a tubular construct. 6 EHTs (FIG. 9C) were cut open and layered to form a contracting network. 3 EHTs (FIG. 9D) were twirled together to form a longitudinal "rope" structure. Bars: 10 mm;

FIG. 10 shows a holding device which may be employed for the method for preparing a multiring engineered heart tissue construct according to the invention, in particular an embodiment of a suspension device for suspending a star-shaped multiring EHT construct. There are two semi-annular brackets. Each bracket comprises five suspension means, in this example in the form of pins. Two opposing pins or suspension means, one on each of the two brackets serve to suspend one engineered heart tissue ring. The two brackets are connected to each other by two springs. The two brackets may be moved closer with respect to each other against the force of the two springs. The dimensions of the brackets and the positions of the suspension means located thereon are chosen such that suspension of the engineered heart tissue rings is accompanied by movement of the two opposing brackets closer to each other so that the rings are suspended under a tensile load created by the springs located inbetween the brackets. In alternative arrangements each suspension means could be mounted separately and a spring could be located between a pair of opposing suspension means or pins in order to create a bias for suspending a engineered heart tissue ring under tensile load around the pair of suspension means. The engineered heart tissue rings are subjected by the suspension device and can be adjusted by properly using the spring or springs acting between opposing suspension means.

FIG. 11 shows the composition of a serum-free culture medium which can be used for culturing cardiac myocytes and EHTs under chemically defined conditions. The medium comprises several growth factors added as supplements. The skilled person will understand that one or more of these growth factors may be replaced against other growth factors or even omitted from the medium without any adverse effect on the growth of cardiac myocytes or the formation of EHTs.

EXAMPLES

Experimental animals were maintained in accordance with the guiding principles of the American Physiological Society. Data are presented as mean±standard error of the mean or box plots with mean and 95% confidence interval. Statistical differences were determined using paired and unpaired two-tailed Student's t-tests (in vivo data), repeated ANOVA (in vitro contraction experiment), or Mann-U-Whitney test (mapping). A P value of <0.05 was considered statistically significant.

Example 1

ETH Construction from Cardiac Myocytes of Neonatal Rats

EHTs were constructed as previously described in Zimmermann, W. H. et al., Circulation 106, I 151-7 (2002) and published International Application WO 01/55297. Briefly, EHT rings (reconstitution volume: 0.9 ml) were prepared by mixing isolated heart cells from neonatal rats ($2.5 \times 10^6$ cells/EHT) with collagen type I from rat tails (0.8 mg/EHT; pH adjusted to physiologic values −7.4 with 0.1 N NaOH), serum-containing culture medium (2×DMEM, 20% horse serum, 4% chick embryo extract, 200 U/mL penicillin, and 200 mg/mL streptomycin; similar volume as neutralized collagen), and Engelbreth-Holm-Swarm tumor exudate ("Matrigel" final concentration 10% v/v; tebu, France).

Figure 1A:
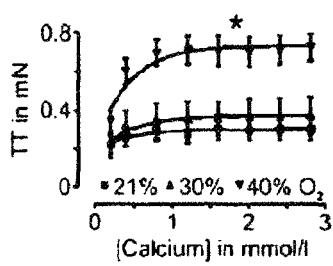
FIGS. 1A-1F show the influence of the present amount of oxygen (FIG. 1A) of the applied load (FIG. 1B) and of the amount of insulin present (FIG. 1C) as well as a single EHT ring (FIG. 1D) a multiring engineered heart tissue construct suspended in a suspension device (FIG. 1E) and the resulting multiring heart tissue construct (FIG. 1F)
Figure 1B:
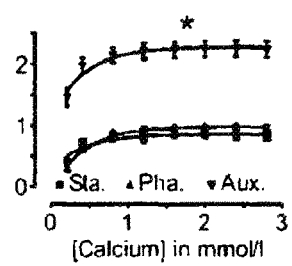
Figure 1C:
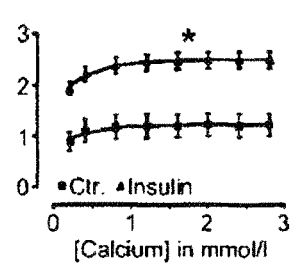
Figure 1D:
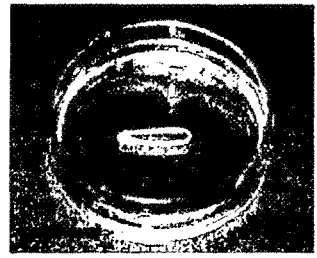
Figure 1E:
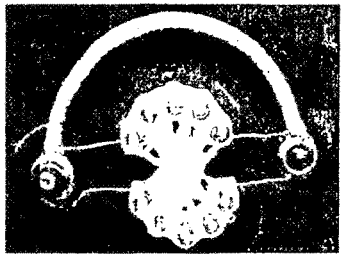
Figure 1F:
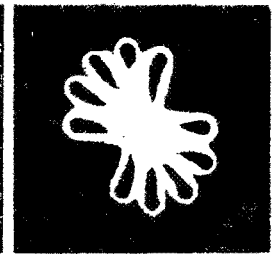

EHTs were transferred after 7 days of culturing in casting molds onto custom made stretch devices to facilitate static (110% of slack length), phasic (from 100 to 110% of slack length at 2 Hz), or auxotonic (culture on deflection coils at 110% of slack length adjusted to deflect 1 mm at 1-1.5 mN) loading. Static loading denotes a condition of constant strain induced by its lateral attachment to stable holders. Phasic load is imposed on EHTs by attaching EHTs to mobile (e.g. motor driven) lateral holders that are forced to move apart to defined positions with a defined frequency. Auxotonic loading conditions are installed by attaching the EHTs to lateral deflection coils adjusted to be deflected towards a defined condition by a defined force. Taken together (1) the lateral distance can be permanently adjusted within a variable range at a defined time range to achieve static loading; (2) the lateral distance of EHTs can be adjusted within a variable range at a defined time under phasic load; (3) the lateral distance of EHTs can be adjusted to a defined yet variable position depending on the intrinsic contractile activity (force and frequency) by auxotonic loading. Contractile parameters were analyzed by isometric contraction experiments of single loop EHTs as described in Zimmermann, W. H. et al., Circulation 106, I 151-7 (2002) and published international application WO 01/55297. Multi-loop EHTs were generated by stacking single circular EHTs. 5 EHTs (each with an outer/inner diameter −10/8 mm; FIG. 1d) were stacked in a crosswise manner on a specially designed holding device (FIG. 1e) and incubated in the above medium (DMEM, 10% horse serum, 2% chick embryo extract, 100 U/mL penicillin, and 100 mg/mL streptomycin) under standard conditions (37° C., 5-101 $CO_2$, 21-40% $O_2$) in a holding device according to the invention. Under these conditions circular EHTs fused and formed contracting multiring EHT constructs (diameter −15 mm, thickness: 1-4 mm; FIG. 1f). Non-contractile grafts for control purposes were constructed according to the EHT protocol described in Zimmermann, W. H. et al., Circ Res 90, 223-30 (2002) Instead of freshly isolated heart cells rat cardiac non-myocytes (n=3) or vascular smooth muscle cells (n=2) were used.

In course of the invention, it was found that three modifications of the original reconstitution protocol described in Zimmermann, W. H. et al., Circ Res 90, 223-30 (2002); Fink, C. et al., Faseb J 14, 669-79 (2000) and in the published International Application WO 01/55297 enhanced contracting characteristics of the resulting EHTs: (1) Increasing ambience oxygen from 21% to 40% (FIG. 1a), (2) culture under conditions that allow active contractions and relaxation (auxotonic strain; FIG. 1b), and (3) supplementation of the culture medium with 10 pg/ml insulin (FIG. 1c). The use of insulin together with triiodothyronine (1 nM) enabled construction of EHT without Matrigel.

Example 2

Infarct Model and Grafting

The potential of multiring EHT constructs to repair diseased hearts in male Wistar rats with myocardial infarcts was tested. Myocardial infarctions were generated in ventilated, isoflurane (2%) anesthetized male Wistar rats (318+3 g; n=121) by permanent ligation of the left anterior descending coronary artery (LAD ligation; 5-0, Prolene, Ethicon, Germany). 14 days after LAD ligation (first surgery) an independent and blinded investigator evaluated infarct localization and size by Echocardiography (ECHO).

Echocardiography was performed in volatile isoflurane (2%) anaesthesia as described previously with a HP Sonos 7500 System (Philips, Amsterdam, The Netherlands) equipped with a 15 MHz linear array transducer (Zimmermann, W. H. et al., Circulation 106, I 151-7 (2002)). To monitor changes in myocardial performance all animals were subjected to ECHO 14 days post LAD ligation and again 4 weeks after grafting or Sham-operation (longitudinal study design). Additionally, baseline function and dimensions in healthy age-matched Wistar rats (n=29) were evaluated. ECHO recordings and analyses were performed by blinded investigators. Inter- and intraobserver variation of reported data was <10%.

Given the well-known variability of infarct size after LAD ligation in rodent models, a transmural infarction with a fractional area shortening (FAS) of less than 40% was defined as inclusion criterion (FAS of −60% was detected in 29 healthy Wistar rats of comparable age). Multiring EHT constructs were implanted 2 weeks after infarct induction by suturing multir-ing EHT constructs onto the epicardium (6 single knots; 5-0, Prolene, Ethicon, Germany). Fixation on healthy myocardium was ensured while the center of the multiring EHT construct was arranged above the infarct. In the Sham group, sutures were placed as if multiring EHT constructs were implanted. All animals received immunosuppressants as described previously in Zimmermann, W. H. et al., Circulation 106, I 151-7 (2002), i.e. azathioprine: 2 mg/kg bodyweight/day, ciclosporin A: 5 mg/kg bodyweight/day, methylprednisolone: 5 mg/kg bodyweight/day.

51 rats did not survive the LAD ligation, 19 rats did not display any functional deficits, and 10 rats had a FAS >40% after LAD ligation. Eventually, 41 rats (FAS <40%) were subjected to engraftment (n=24; FIG. 2a) or Sham operation (n=17). 4 from 24 (EHT group) and 2 from 17 (Sham group) rats died during the second surgery. Two additional rats from the EHT group died during the 4 week study phase after the second surgery. Hence, 18 and 15 animals from EHT and Sham groups, respectively, survived the complete study duration. These animals were subjected to epicardial mapping, echocardiography, magnetic resonance imaging, LV catheterization and morphological studies 4 weeks after the second surgery.

Example 3

Epicardial Mapping

Electrical coupling of multiring EHT constructs to the host myocardium was assessed 4 weeks after engraftment by high resolution epicardial mapping as described in Dhein, S. et al., Circulation 87, 617-30 (1993). Briefly, hearts were excised and Langendorff-perfused with Tyrode's solution at a constant pressure of 70 cm H$_2$O and 37° C. Unipolar ECGs were recorded simultaneously from 256 AgCl electrodes (interelectrode distance: 1 mm; sampling rate: 4 kHz/electrode; HALO system; P. Rutten, Hamburg, Germany) arranged in 4 polyester blocks around the circumference of spontaneously beating hearts. Activation time was determined at each electrode and the spread of excitation was analyzed by constructing isochrones. For quantitative analysis the total activation time assessed as the delay between activation of the first and activation of the last electrode for each region under investigation was determined.

Figure 4A:
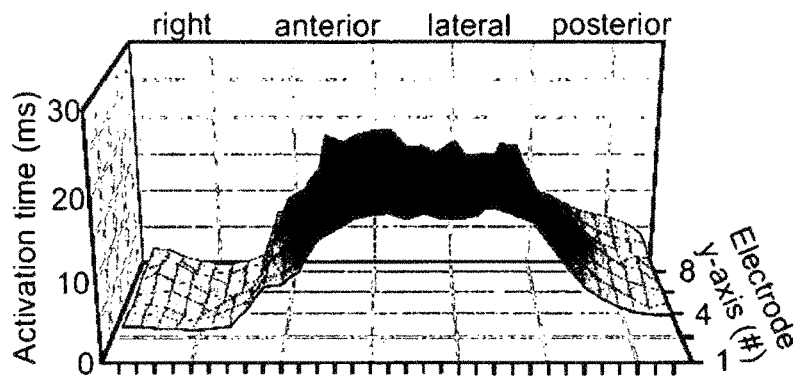
FIGS. 4A-4C show the epicardial activation time in the area of infraction (FIG. 4A) and in hearts with grafts (FIG. 4B), and the total activation time in right, anterior, lateral and posterior segments of the hearts (FIG. 4C)
Figure 4B:
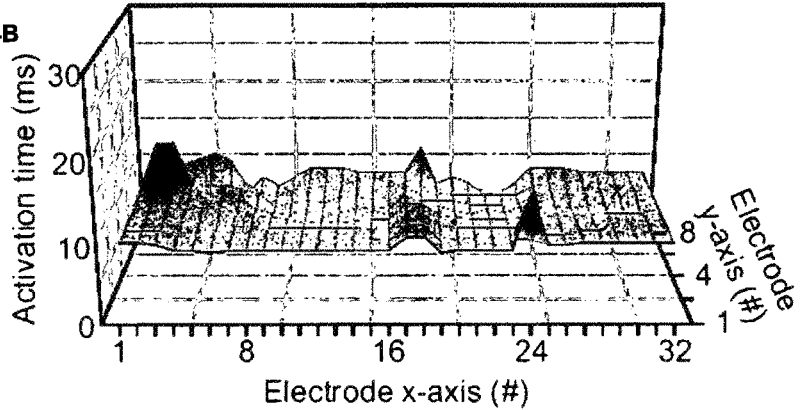
Figure 4C:
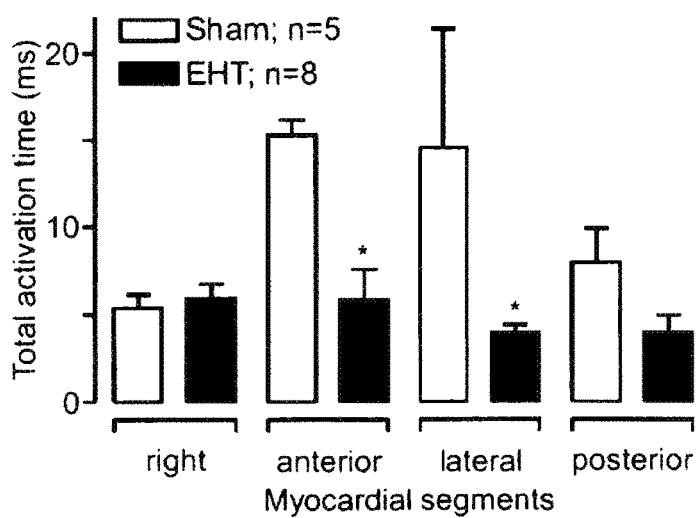

Sham animals (n=5) demonstrated the expected delay of impulse propagation in infarcted areas (FIGS. 4A and 4C). In contrast, epicardial activation was normal in rats that received multiring EHT construct grafts (n=8), indicating undelayed anterograde coupling of multiring EHT constructs to the host myocardium (FIGS. 4B-4C). In addition, the epicardial activation in animals that received non-contractile grafts containing either rat fibroblasts (n=2) or smooth muscle cells (n=2) was studied. Here, similar conduction deficits as in the Sham group were observed, i.e. an activation delay of 10 to 18 ms in the lateral wall and no active responses in most areas of the fibro-blast/smooth muscle cell containing grafts.

Example 4

Functional Consequences of Grafting

Prior to our grafting studies, myocardial dimension and function were assessed in an independent healthy age-matched control group by ECHO (n.29), MRI (n=29) and CATH (n=6). ECHO was performed as outlined above. Eventually, ECHO was performed 14 days after LAD ligation in all rats that survived the first surgery (n=70). 33 animals survived the complete study and were subjected to ECHO (in 33 from 33 animals), MRI (in 28 from 33 animals), and CATH (in 14 from 33 animals) 28 days after the second surgery. The results are depicted in FIGS. 7A-7C Magnetic resonance imaging was performed in volatile isoflurane (2%) anaesthesia with a Bruker 4.7T Biospect System using a fast gradient echo sequence with TR 21 ms, TE 5 ms and a flip angle of 30 degrees. Recordings were ECG- and breath triggered. A total of 6-8 subsequent movie frames were acquired with 256×128 pixels at 200×400 μm pixel resolution. A longitudinal view was obtained for orientation purposes. Based on the latter 20-30 cross sections (short axis) from apex to base were imaged (4D cine movie). Subsequently, datasets were subjected to off-line analysis with manual segmentation of the heart contours. Examiners were blinded to the study protocol.

For LV-catheterization, pressure-volume loops were recorded under isoflurane (2%) anaesthesia with a Millar 2 Fr catheter (model: SPR-838) connected to Aria/PowerLab data acquisition hardware (Millar/PowerLab) by a blinded investigator. Volume calibration was performed by equating catheter-recorded minimal and maximal conductance with minimal and maximal MRI-volumes, respectively. All data were analyzed off line with PVAN 3.2 software (Millar) by a second blinded investigator.

Figure 5A:
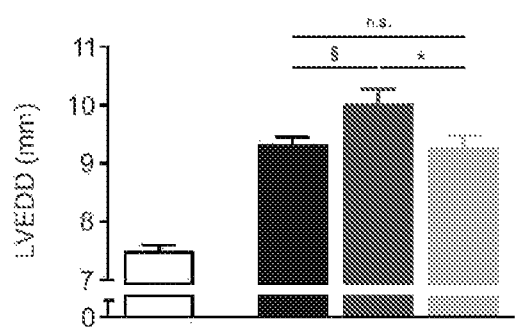
FIGS. 5A-5F show the changes in left ventricular function after multiring EHT construct implantation for various parameters.
Figure 5B:
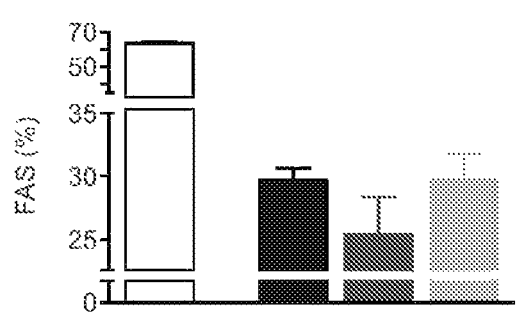
Figure 5C:
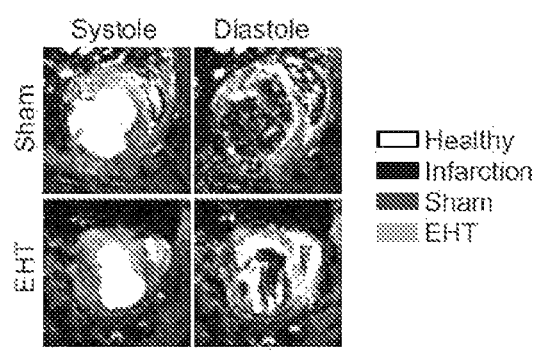
Figure 5D:
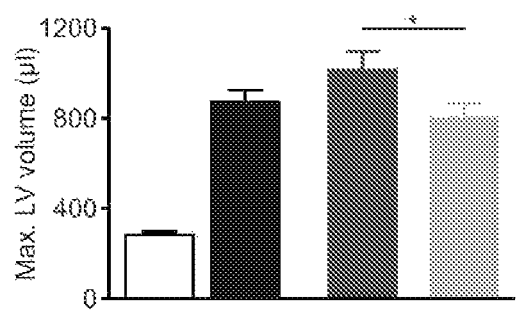
Figure 5E:
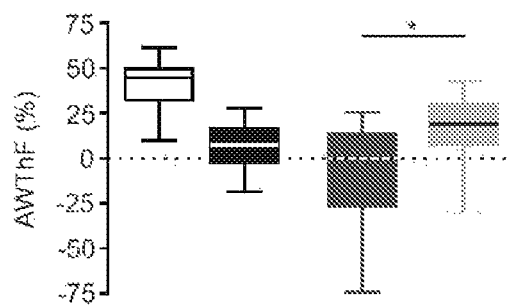
Figure 5F:
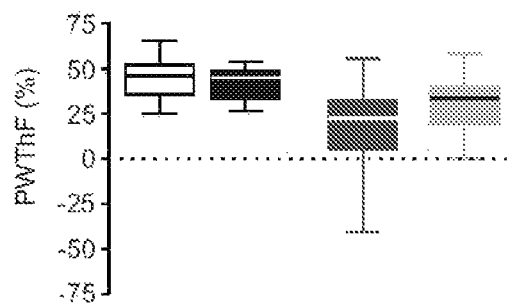
Figure 6A:
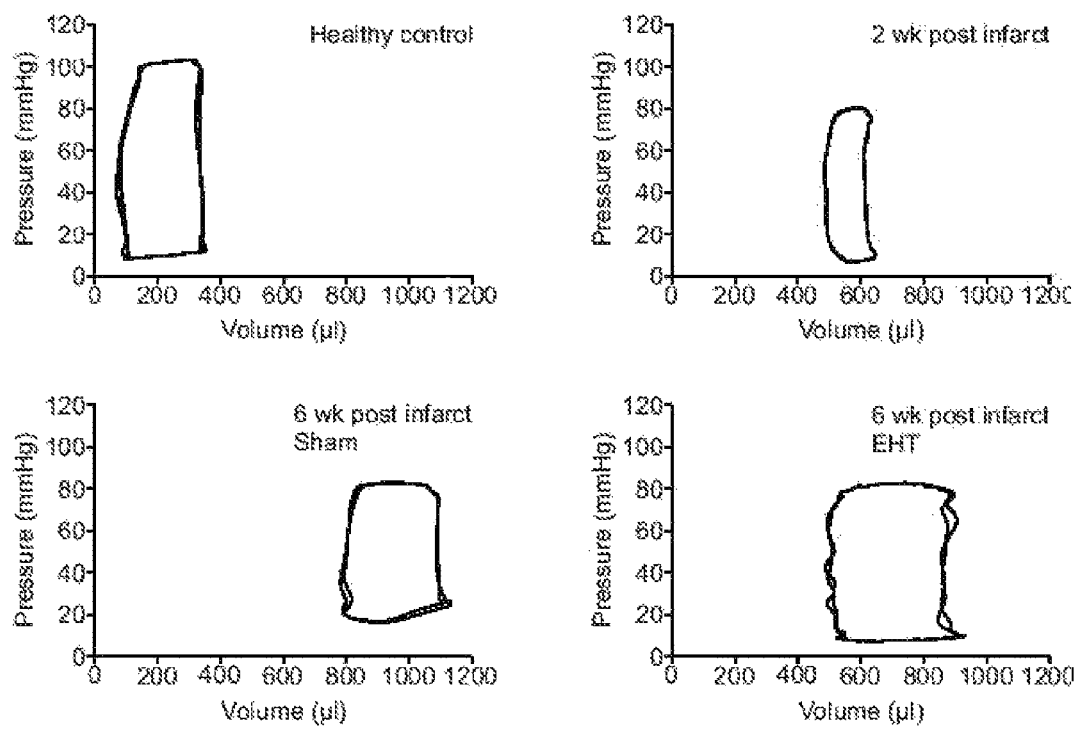
FIGS. 6A-6D show the influence of multiring EHT construct grafting on left ventricular hemodynamics for various parameters.
Figure 6B:
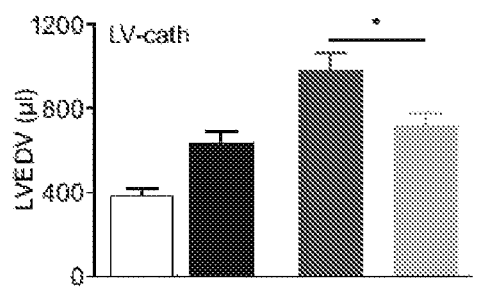
Figure 6C:
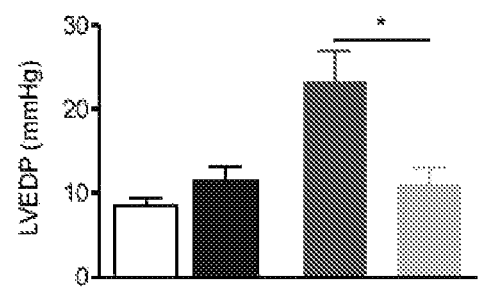
Figure 6D:
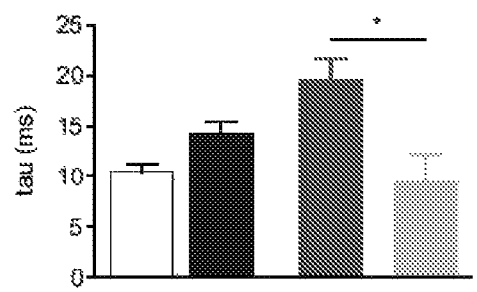
Figure 8A:
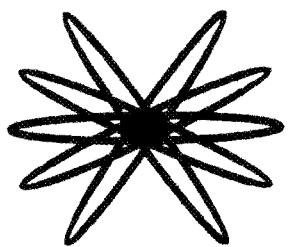
FIGS. 8A-8C show schematic representations of different geometries of multiring EHT constructs according to the invention.
Figure 8C:
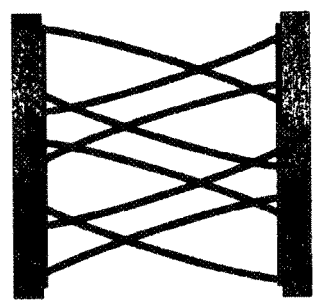
Figure 8B:
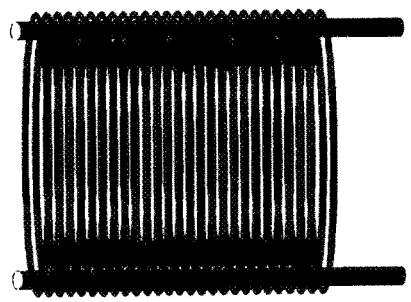
Figure 9A:
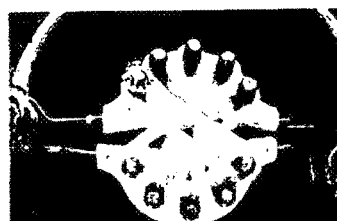
FIG. 9A-9D show the generation of different EHT geometries prepared in the course of the invention.
Figure 9B:
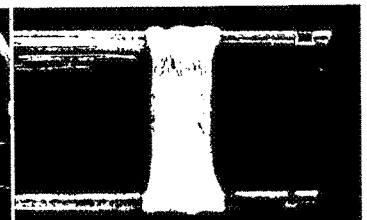
Figure 9C:
Figure 9D:
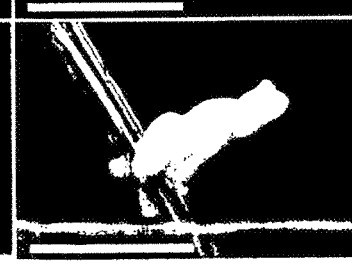
Figure 10:
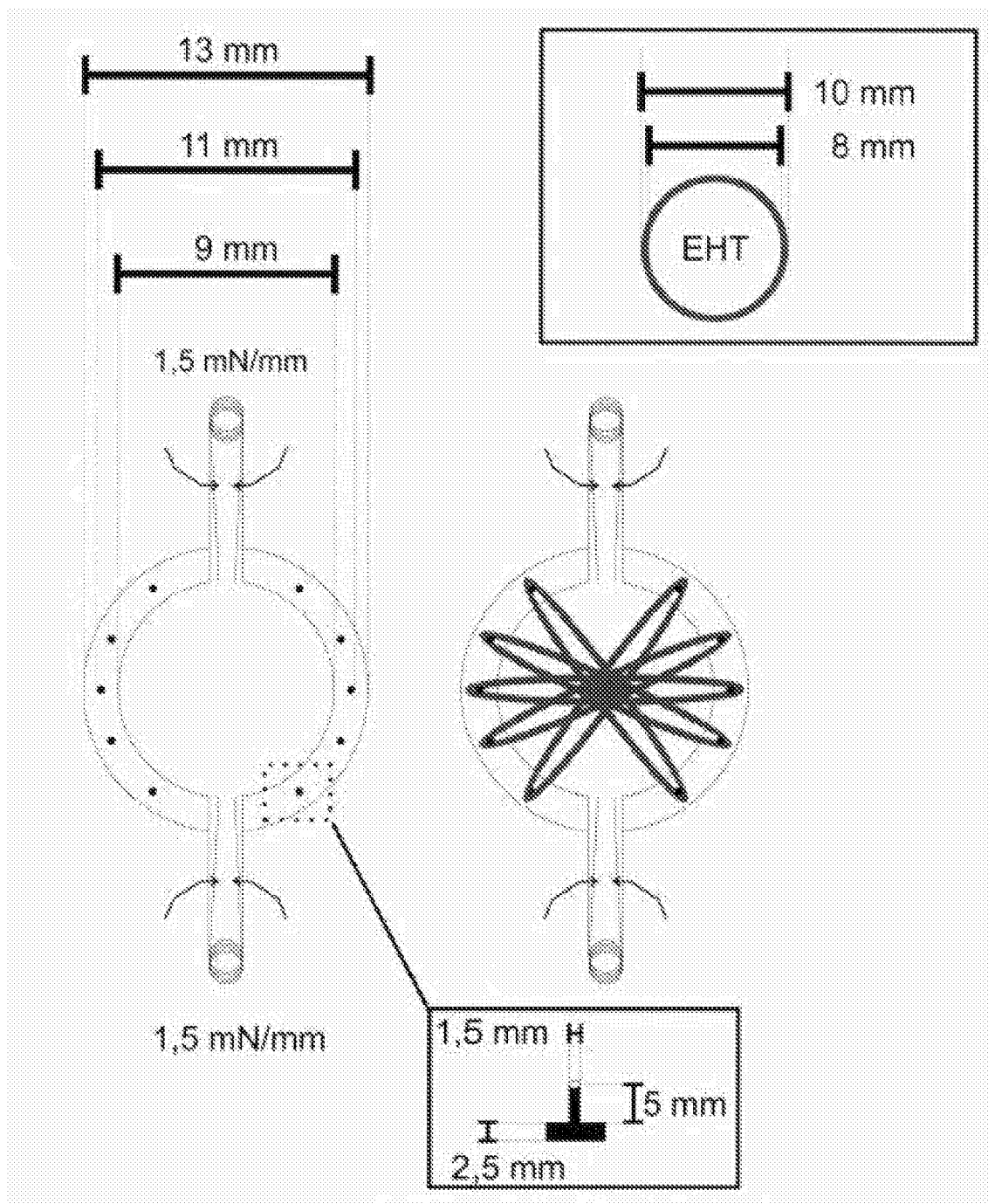
FIG. 10 shows a holding device which may be employed for suspending a multiring EHT construct while carrying out the invention.

In contrast to ECHO (longitudinal study design), it was refrained from repeated MRI and CATH due to high mortality of animals that underwent multiple 4D CINE mode MRI (1-2 hours imaging time under anaesthesia) and the availability of only one defined access to the left ventricle through the right carotid artery for CATH under closed chest conditions. Evaluation 14 days after infarction revealed marked enlargement of left ventricle dimension and volume (FIGS. 5A and 5D; FIG. 6B), a reduced fractional area shortening (FAS; FIG. 5B), a decreased anterior wall thickening fraction (AWThF; FIG. 5E) without notable effects on the posterior wall thickening fraction (PWThF; FIG. 5F), and a rightward shift of the pressure-volume relationship (FIG. 6A). At the same time, left ventricular enddiastolic pressure (LVEDP; FIG. 6C) and tau (index of relaxation; FIG. 6d) remained almost normal indicating that the experimental animals were in a compensated state of heart failure prior to the second surgery (FIG. 7A-7C). 28 days later, ECHO, MRI, and CATH data collectively indicated further deterioration in Sham operated animals (FIGS. 5A-5F and 6A-6D; FIG. 7A-7C). In particular, left ventricular end diastolic dimensions (LVEDD) increased (FIG. 5A) and FAS slightly decreased (GIF. 5B). Moreover, LVEDP and tau increased markedly to >20 mmHg and 20 ms, respectively (FIGS. 6C-6D). In contrast, left ventricle dimensions and FAS remained unchanged in animals from the EHT group, i.e. they did not differ from baseline values 2 weeks after LAD ligation (FIG. 5A-5B). Whereas ECHO examination did not allow for unambiguous identification of volumes and active systolic thickening of the ventricular wall, the higher spatial resolution of MRI enabled us to precisely visualize left ventricular volumes (from multiplane images and offline 3D rendering of the total ventricle) and systolic wall thickening in anterior (area of infarct) and posterior (no infarct) segments of the left ventricle (FIGS. 5C-5F). MRI supported the ECHO data and showed significantly smaller left ventricular volumes in the EHT group when compared to Sham animals (FIG. 5D). In addition, MRI demonstrated a significantly improved AWThF (FIG. 5E), whereas PWThF was not affected (FIG. 5F). To assess whether non-myocytes or the plain physical influence of multiring EHT construct grafting might have contributed to the improvement of AWThF, the effect of non-contractile fibroblast (n=3) and smooth muscle cell grafts (n=2) was studied. As in the Sham group and in contrast to the EHT group AWThF was markedly reduced (−3±7%) and PWThF was not affected (31+131) in animals that received non-contractile grafts (pooled data; n=5). CATH allowed for detailed analysis of hemodynamic function with superior temporal resolution (FIGS. 6A-6D). Pressure-volume loop analysis supported the former data showing that left ventricular dilatation was less after multiring EHT construct engraftment than after Sham surgery (FIG. 6B). Most strikingly, LVEDP and tau in rats with grafts did not differ from healthy controls (FIGS. 6C-6 D).

Example 5

Multiring EHT Construct In Vivo Morphology after Grafting

Four weeks after grafting, multiring EHT constructs could readily be identified by its distinct appearance and location (FIGS. 2B-2C). The pale color indicated that the multiring EHT construct retained a high connective tissue content. Hearts were fixed in neutral buffered 4W formaldehyde/1% methanol, pH 7.4 and subjected to histological analysis as described previously in Zimmermann, W. H. et al., Circulation 106, I 151-7 (2002). Briefly, paraffin embedded sections (4 μm) were stained with hematoxylin and eosin (H&E; see FIGS. 2A-2F). Cryo-sections (10 μm) were stained with phalloidin-Alexa 488 to label f-actin and antibodies directed against a-sarcomeric actinin (1:1000;

Sigma) and ED2 (full strength; Serotec) with appropriate secondary antibodies (see FIGS. 3A-3K).

H&E staining of paraffin sections revealed formation of compact and well differentiated multiring EHT construct-derived heart muscle covering the infarcted myocardium (FIGS. 2D-2F). Notably, the reconstituted myocardium was oriented along the circumference of the heart and consisted of multiple cell layers with a total diameter of up to 1000 µm (FIG. 2E), a thickness never observed during in vitro culture.

Figure 3A:
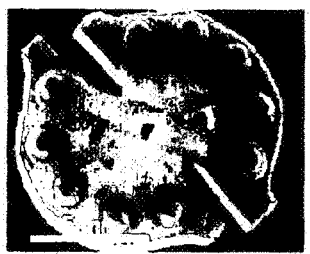
FIGS. 3A-3K show the identification of grafted cells by in vitro DAPI labelling.
Figure 3B:
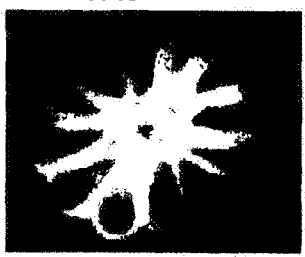
Figure 3C:
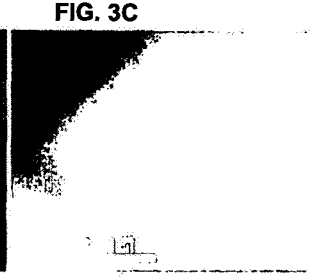
Figure 3D:
Figure 3E:
Figure 3F:
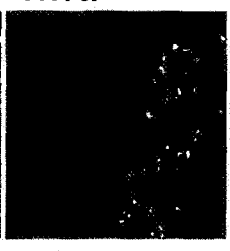
Figure 3G:
Figure 3H:
Figure 3I:
Figure 3J:
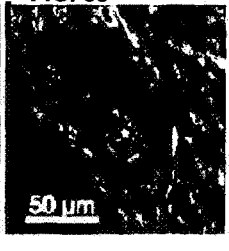
Figure 3K:

To further evaluate whether cardiac myocytes within the reconstituted myocardium were of donor origin, multiring EHT constructs (n=5) were labelled with DAPI (1 dig/ml) prior to implantation (FIGS. 3A-3C) and searched for DAPI-positive cells after additional 4 weeks. Engrafted multiring EHT constructs could be clearly distinguished from the recipient's myocardium by the blue fluorescence of the DAPI-labelled nuclei (FIG. 3D-3G). In high power magnification, it was observed that multiring EHT construct-derived cardiac myocytes developed a differentiated and well organized phenotype including in registry organization of sarcomeres (FIG. 3H). DAPI-positive cardiac myocytes were not observed in the host myocardium. DAPI-negative cardiac myocytes were not noticed within the graft. Besides cardiac myocytes, many non-myocytes showed blue nuclei (FIGS. 3I-3K). Interestingly, blood vessels in the grafts contained cells with blue nuclei, suggesting donor-origin (FIGS. 3I-3K). The presence of erythrocytes proved connection of these vessels to the recipient's vasculature (FIG. 3K).

Example 6

ETH Construction from Human Embryonic Stem Cells

1. Suitable ES Cell Lines

Pluripotent human embryonic cell lines have been established and can be commercially obtained from different providers. These cell lines have been listed by the US National Institutes of Health (Bethesda, Md., USA), from which further information as to the cell line characteristics and providers may be obtained. The following ES cell lines are available and may be used for preparing EHTs: cell lines hESBGN-01, hESBGN-02, hESBGN-03 from BresGen, Inc. (Athens, USA), NIH Code: B001, BG02, BG03; cell lines Sahlgrenska 1, Sahlgrenska 2 from Cellartis AB (Goteborg, Sweden), NIH Code: SA01, SA02; cell lines HES-1, HES-2, HES-3, HES-4, HES-5, HES-6 from ES Cell International (Singapore), NIH Code: ES01, ES02, ES03, ESO4, ES05, ES06; cell line Miz-hES1 from the Medical Research Center, MizMedi Hospital (Seoul, Korea), NIH Code: MI01; cell lines I 3, I 3.2, I 3.3, I 4, I 6, I 6.2, J 3, J 3.2 from the Rambam Medical Center (Haifa, Israel), NIH Code: TE03, TE32, TE33, TE04, TE06, TE62, TE07, TE72; cell lines HSF-1, HSF-6 from the University of California, Department of Obstetrics, Gynecology & Reproductive Sciences (San Francisco, USA), NIH Code: UC01, UC06; cell lines H1, H7, H9, H13, H14 from the Wisconsin Alumni Research Foundation (Madison, USA), NIH Code: WA01, WA07, WA09, WA13, WA14.

Different groups have shown that human embryonic stem cell lines WA01 (H1), WA07 (H7), WA09 (H9) including subclones H9.1, H9.2 and ES02 can differentiate either spontaneously or if co-cultured with visceral-endoderm like cells (END-2) or liver parenchymal carcinoma cells (HepG2) into cardiac myocytes (Xu, C., et al. Characterization and enrichment of cardiac myocytes derived from human embryonic stem cells. Circ Res 91, 501-8 (2002); Kehat, I. et al. supra; Mummery, C. et al. Differentiation of human embryonic stem cells to cardiac myocytes: role of co-culture with visceral endoderm-like cells. Circulation 107, 2733-40 (2003)). However, the propensity of mammalian embryonic stem cells to differentiate into cardiac myocytes is an inherent trait of all true embryonic stem cells and thus not limited to the above mentioned cell lines. Apart from embryonic cells, other stem cells may be used for preparing the EHT rings or multiring constructs according to the invention. Such stem cells include, but are not limited to, human pluripotent adult stem cells with a propensity to give rise to cardiac myocytes (e.g. c-kit positive cells (Beltrami et al. Cell 2003), endothelial progenitor cells (Badorff et al. Circ Res 2002), side population cells (Jackson et al. JCI 200x), Sca-1 positive cells (Oh et al. 2002), Is1-1 positive cells (Laugwitz et al. 2005). These cells may be derived from the blood, bone marrow or from various organs including the heart, the liver, umbilical cord, placenta, fat tissue, among others.

It is particularly preferred to employ genetically modified human embryonic stem cells for reconstitution of EHTs, e.g. cells capable of expressing proteins that allow selection of cardiac myocytes and/or depletion of non-myocytes. By selecting ES, homogenous cell populations can be formed which may again be substituted with defined and also selectable non-myocytes which include but are not limited to endothelial cells, fibroblasts, smooth muscle cells, and macrophages within the EHT rings. Moreover, selection allows for depletion of tumorigenic cells which is a prerequisite for the use of the EHTs in therapeutic approaches. Selection can be performed before or simultaneously with culturing the cells in casting molds. For instance, in vitro-differentiation may be performed directly after propagation of the ES cells and the resulting embryonic stem cell derived cardiac myocytes can be subjected to selection before reconstituting the EHTs. Alternatively, undifferentiated embryonic stem cells are propagated and used for the preparation of EHT rings or multiring EHT constructs and selection is performed on the EHT constructs at a later stage. Preferably, selection is to be performed after the EHT rings or the multiring EHT constructs have been formed.

Selection may be achieved by stable introduction of selectable marker genes. The expression of such genes is controlled either by a cardiac myocyte specific promoter (positive selection) or a non-myocyte specific promoter (negative selection) into embryonic stem cells. These may be but are not limited to:

amino-3' glycosyl phosphotransferase conferring a neomycin resistance [neoR]

herpes simplex virus thymidine kinase [TK] which transforms ganciclovir into a cytotoxic triphosphate purine nucleoside phosphorylase [PNP] from *Escherichia coli* which converts fludarabine to toxic fluoro-ATP fluorescing proteins and P-galactosidase which facilitate optical identification Expression of neoR, fluorescing proteins, or P-galactosidase under the control of a cardiac myocyte specific promoter, e.g. α-myosin heavy chain promoter (see Klug, M. G., Soonpaa, M. H., Koh, G. Y. & Field, L. J. Genetically selected cardiac myocytes from differentiating embryonic stem cells form stable intracardiac grafts. J Clin Invest 98, 216-24 (1996)), myosin light chain 2v promoter (see Muller, M. et al. Selection of ventricular-like cardiac myocytes from ES cells in vitro. Faseb J 14, 2540-8 (2000)) enable positive selection of cardiac myocytes by eliminating non-myocytes either through addition of cytotoxic G418 or fluorescence activated cell sorting (FAGS). The techniques for selection are well known to the person of skill. Alternatively, non-myocytes expressing TK or PNP under the control of a promoter that is not active in cardiac myocytes, e.g. the Oct-4 promoter (Boiani, M., Kehler, J. & Scholer, H. R. Activity of the germline-specific Oct4-GFP transgene in normal and clone mouse embryos. Methods Mol Biol 254, 1-34 (2004)), the Rex-1 promoter (see Hosler, B. A., Rogers, M. B., Kozak, C. A. & Gudas, L. J. An octamer motif contributes to the expression of the retinoic acid-regulated zinc finger gene Rex-1 (Zfp-42) in F9 teratocarcinoma cells. Mol Cell Biol 13, 2919-28 (1993)) can be eliminated (negative selection) by addition of ganciclovir or fludarabine, respectively (Lockett, L. J., Molloy, P. L., Russell, P. J. & Both, G. W. Relative efficiency of tumor cell killing in vitro by two enzyme-prodrug systems delivered by identical adenovirus vectors. Clin Cancer Res 3, 2075-80 (1997)). Genetic modification of human embryonic stem cells is either performed by stable transformation utilizing established lipofection or electroporation protocols to introduce the genetic information (cDNA] into stem cells (see, for example, Nagy, A., Gertsenstein, M., Vintersten, K. & Behringer, R. Manipulating the Mouse Embryo: A Laboratory Manual. (2002); Eiges, R. et al. Establishment of human embryonic stem cell-transfected clones carrying a marker for undifferentiated cells. Curr Biol 11, 514-8 (2001)) or by lentivirus mediated gene transfer leading to stable transduction of embryonic stem cells (see Ma, Y., Ramezani, A., Lewis, R., Hawley, R. G. & Thomson, J. A. High-level sustained transgene expression in human embryonic stem cells using lentiviral vectors. Stem Cells 21, 111-7 (2003)). Integration of the exogenous genetic material is confirmed by standard methods (e.g. southern blotting, polymerase-chain-reaction; see Sambrook, J. & Russell, D. Molecular Cloning: A Laboratory Manual. (2001)).

2. Preparing EHTs from Selectable, Undifferentiated ES Cells

Selectable human embryonic stem cells are used for reconstitution in an undifferentiated state. The undifferentiated human embryonic stem cells are cultured for propagation in Dulbecco's modified Eagle's medium (DMEM) with 20% batch tested fetal calf serum or 20% serum replacement, 1 mM L-glutamine, 0.1 mM P-mercaptoethanol, and 1% nonessential amino acids on mitotically inactivated fibroblast feeders (see Xu, C., et al. supra; Kehat, I. et al., supra) until a sufficient cell number of about $0.1\text{-}10\times10^6$ cells is reached. All substances are provided by several companies including Invitrogen. Human basic-fibroblast growth factor (bFGF, 4 ng/ml) is not essential but may be added to improve maintenance of an undifferentiated state. Antibiotics (100 U/ml penicillin and 100 pg/ml streptomycin) may also be added. Subsequently, undifferentiated selectable embryonic stem cells ($0.1\text{-}10\times10^6$ cells) are mixed with scaffold material (e.g. collagen type I, concentration: 0.51.5 mg/ml) and growth promoting culture medium (see above). The total reconstitution volume consists normally of 0.5-1 ml but may be reduced or increased depending on the respective demand. The reconstitution mixture is filled into casting molds (e.g. the circular molds described in the WO 01/55297) immediately after mixing. Under normal culture conditions (e.g. 37° C., 5-10% $CO_2$, 21-40% $0_2$) solid tissue-like structures will form within 1-10 days. Under these conditions, differentiation of the embryonic stem cells occurs spontaneously and may additionally be affected by exogenous factors (e.g. addition to the culture medium of growth factors and cytokines including insulin, insulin-like growth factor, cardiotrophin-1, bone morphogenic proteins, sonic hedgehog at $EC_{50}$ concentrations). The solid tissue-like structures may optionally be transferred on stretch devices (as described above for the preparation of multiring constructs, or as described in Zimmermann for EHT rings) to optimize culture medium perfusion and impose defined mechanical strain which may be static, phasic, or auxotonic—on the tissue constructs.

Stacking of human multiring engineered heart muscle may be performed as described for the rat model during the differentiation and selection process. EHT rings or multiring EHTs are composed of interconnected muscle strands consisting of interconnected single cardiac myocytes. Cell connections consist of gap junctions staining positive for connexin proteins. Single cardiac myocytes develop organized sarcomeres staining positive for a-sarcomeric actinin and other sarcomeric proteins. The muscle function of EHT rings or multiring EHT constructs can be analyzed by isometric contraction experiments to demonstrate its organotypic responsiveness for example to increasing calcium concentrations (positive inotropic effect) and isoprenaline (positive inotropic and lusitropic effects).

Positive or negative selection (see above) may be performed after formation of contractile areas within the EHT rings i.e. 5-30 days after casting of the reconstitution mixture into the molds. Alternatively, selection may be performed after the rings have been transferred to the stretching device or during stacking for preparing the multiring EHT construct. Selection may be performed until optimal tissue structure and function has developed (e.g. 10-40 days depending on the observed effect). Selection may be achieved by addition of a defined pharmacological agent (e.g. G418, ganciclovir, fludarabine) into the culture medium).

3. Preparing EHTs from ES-Derived Cardiac Myocytes

For the preparation of EHTs from human cells, we utilized cardiac myocytes derived from an established human embryonic stem cell line (H9, subclone H9.2). However, it is to be understood that all true human and non-human embryonic stem cells can be used for preparing the EHTs of the invention. For example, human embryonic stem cells derived from individual blastomeres (Klimanskaya I, Chung Y, Becker S, Lu S J, 'Lanza R (2006) "Human embryonic stem cell lines derived from single blastomeres", Nature, electronic publication ahead of print on Aug. 23, 2006) or from the inner cell mass of an embryo in the blastocyst stage (Thomson J A et al. (1998), Science 282:1145-7) as well as other multipotent embryonic-stem cell like cells, e.g. from parthenogenetic embryos (Vrana K E et al. (2003), Proc Natl Acad Sci USA, 100 Suppl 1:11911-6), adult germline stem cells (Guan K et al. (2006), Nature 440:1199203), somatic nuclear transfer derived embryos (Wakayama T et al. (2001), Science 292:740-3) or reprogrammed somatic cells (Cowan C A, et al. (2005), Science 309:1369-7; Takahashi K and Yamanaka S (2006), Cell 126:663-76) can be used. Similarly, somatic stem cells (Badorff C, et al. (2003), Circulation 107:1024-32; Beltrami A P, et al. (2003), Cell 114:763-76; Dimmeler S, et al. (2005); J Clin Invest 115:572-83; Murry C E, et al. (2005), Circulation 112:3174-83) with a cardiogenic potential are applicable in EHT construction as outlined for embryonic stem cells. Embryonic stem cell derived cardiac myocytes were selected by micro-dissection after spontaneous differentiation in vitro. Differentiation was performed in suspension culture, and the cells were subsequently plated on gelatine coated culture dishes as previously described by Kehat, I. et al., J Clin Invest 108, 407-14 (2001). Beating clusters containing embryonic stem cell derived cardiac myocytes were excised with a sharp, sterile glass or plastic pipette. Prior to reconstitution, ES-cell derived cardiac myocytes were enzymatically dispersed in collagenase IV (Life Technologies Inc., 1 mg/ml for 20 min) or with trypsin/EDTA. ES-cell derived cardiac myocytes ($10.000$-$15 \times 10^6$ dispersed cells/500 pl reconstitution mix, preferably 20.000-250.000 dispersed cells/500 pl reconstitution mix) were reconstituted with collagen, Ma-trigel and culture medium according to the established protocol by Zimmermann W. H. et al., Circ Res 90, 223-30 (2002) and WO 01/55297, with the exemption that the following culture medium was used: DMEM (preferably containing 80% knock-out DMEM [no-pyruvate, high-glucose formulation; Life Technologies, Inc.]), 20% fetal calf serum, 1 mM glutamine, 0.1 mM p-mercaptoethanol, 1W non-essential amino acids. Matrigel can be replaced by a mixture of triidothyronine (1 nM) and insulin (10 pg/ml). The EHT reconstitution mixture was pipetted into circular casting molds as described and the mixture was incubated to allow hardening. First contractions of single cardiac myocytes were observed after 24 hours of human EHT (hEHT) culture, larger cell accumulations within hEHTs started to contract synchronously after approx. 1-3 days whereas in unison contractions of whole EHTs with 1-2 Hz were observed after approx. 2-10 culture days.

The invention claimed is:

1. A device for preparing a multiring engineered heart tissue construct, comprising a plurality of associated suspension means for suspending force-generating engineered heart tissue rings under tensile stress, wherein at least one of each of the associated suspension means is resiliently biased so that the suspended force-generating engineered heart tissue ring is able to contract against the bias force provided by the suspension means, wherein the suspension means are arranged to each other so that each force-generating engineered heart tissue ring has one or more contact points to an adjacent force-generating engineered heart tissue ring when suspended in the device.

2. The device of claim 1, wherein two suspension means are associated to each other.

3. The device of claim 2, wherein all associated suspension means are resiliently biased.

4. The device of claim 2, wherein at least one of the two suspension means can be adjusted to vary the tensile stress.

5. The device of claim 2, wherein the associated suspension means are arranged to each other so that the force-generating engineered heart tissue rings can be suspended by stacking to form a central region in which the force-generating engineered heart tissue rings overlap with each other.

6. The device of claim 1, wherein all associated suspension means are resiliently biased.

7. The device of claim 6, wherein the associated suspension means are arranged to each other so that the force-generating engineered heart tissue rings can be suspended by stacking to form a central region in which the force-generating engineered heart tissue rings overlap with each other.

8. The device of claim 1, wherein the at least one suspension means can be adjusted to vary the tensile stress.

9. The device of claim 1, wherein the associated suspension means are arranged to each other so that the force-generating engineered heart tissue rings can be suspended by stacking to form a central region in which the force-generating engineered heart tissue rings overlap with each other.

* * * * *